(12) United States Patent
Combs et al.

(10) Patent No.: US 8,501,493 B2
(45) Date of Patent: Aug. 6, 2013

(54) METHOD FOR MEASURING FIBER DIGESTIBILITY

(75) Inventors: David Kenneth Combs, Verona, WI (US); John Phillip Goeser, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 547 days.

(21) Appl. No.: 12/405,650

(22) Filed: Mar. 17, 2009

(65) Prior Publication Data

US 2009/0272889 A1    Nov. 5, 2009

Related U.S. Application Data

(60) Provisional application No. 61/120,981, filed on Dec. 9, 2008, provisional application No. 61/037,165, filed on Mar. 17, 2008.

(51) Int. Cl.
*G01N 21/00* (2006.01)

(52) U.S. Cl.
USPC ............... 436/164; 436/17; 436/50; 426/623; 426/630; 426/636

(58) Field of Classification Search
None
See application file for complete search history.

(56) References Cited

PUBLICATIONS

Nelson, B. D., et al. Factors affecting the variability of an in vitro rumen fermentation technique for estimating forge quality, 1969, Journal of Dairy Science, vol. 55(3), pp. 358-366.*

Stuth, Jerry, et al. Direct and indirect means of predicting forge quality through near infrared reflectance spectroscopy, 2003, Field Crops Research, vol. 84, pp. 45-56.*

Morgavi, Diego P, et al. Prevention of patulin toxicity on rumen microbial fermentation by SH-containing reducing agents, 2003, Journal of Agriculture Food Chemistry, vol. 51(23), pp. 6906-6910.*

Starter, Making a Starter, 2002, retrieved from internet: http//web.archive.org/web/20020920202020/http://www.alsand.com/beer/yeast/start-E.html.*

Abrams et al. (1987) "Determination of forage quality by near-infrared reflectance spectroscopy—efficacy of broad-based calibration equations," *J. Dairy Sci.* 70:806-813.

Adesogan (2005) "Effect of bag type on the apparent digestibility of feeds in ANKOM Daisy(II) incubators," *Anim. Feed Sci. Technol.* 119: 333-344.

Andres et al. (2005) "Prediction of aspects of neutral detergent fiber digestion of forages by chemical composition and near-infrared reflectance spectroscopy," *Aus. J. Agric. Res.* 56: 187-193.

(Continued)

*Primary Examiner* — Robert Xu
(74) *Attorney, Agent, or Firm* — Joseph T. Leone, Esq.; DeWitt Ross & Stevens S.C.

(57) ABSTRACT

Described is a method of measuring fiber digestion in ruminants and calibrating spectrophotometers using the measured fiber digestion values. The method includes the steps of harvesting rumen fluid from at least one ruminant animal and combining the rumen fluid with a primer composition comprising a carbohydrate. The rumen fluid and carbohydrate are then incubated in a sealed container until a pre-determined pressure is achieved within the sealed container. A plant matter sample is digested with the rumen fluid so treated. The digested sample is the measured for absorbance or reflectance using a spectrophotometer. The digestion values and the absorbance or reflectance values are then correlated to construct a standard curve for predicting fiber digestion values using spectrophotometric analysis, preferably NIRS analysis.

29 Claims, 6 Drawing Sheets

(56) References Cited

PUBLICATIONS

Aastveit and Marum (1993) "Near-infrared reflectance spectroscopy: different strategies for local calibrations in analyses of forage quality," *Appl. Spectroscopy* 47:463-469.

Buxton and Mertens (1991) "Errors in forage-quality data predicted by near infrared reflectance spectroscopy," *Crop Sci.* 31:212-218.

Combs (1998) "Using NIR to Evaluate Forage Quality," *Proc. of the 4-State Forage Feeding and Management Conference, University of Wisconsin-Extension*, 129-135, Madison, Wisconsin.

De Boever et al. (1996) "Prediction of the feeding value of grass silages by chemical parameters, in vitro digestibility and near-infrared reflectance spectroscopy," *Anim. Feed Sci. Tech.* 60:103-115.

Eun et al. (2007) "Use of exogenous fibrolytic enzymes to enhance in vitro fermentation of alfalfa hay and corn silage," *J. Dairy Sci.* 90:1440-1451.

Goering & Van Soest (1970) Forage Fiber Analyses (Apparatus, Reagents, Procedures, and Some Applications) *Agric. Handbook No. 379*, pp. 8-11, ARS-USDA, Washington, DC.

Hall and Mertens (2008) "In vitro fermentation vessel type and method alter fiber digestibility esimates," *J. Dairy Sci.* 91:301-307.

Hoffman et al. (1999) "Prediction of laboratory and in situ protein fractions in legume and grass species using near-infrared reflectance spectroscopy," *J. Dairy Sci.* 82:764-770.

Jung et al. (1998) "Forage quality variation among maize inbreeds: in vitro fiber digestion kinetics and prediction with NIRS," *Crop Sci.* 38:205-210.

Levene (1960) in "Contributions to Probability and Statistics: Essays in Honor of Harold Hotelling," I. Olkin, S. G. Ghurye, W. Hoeffding, W. G. Madow, and H. B. Mann, eds. Stanford University Press, Stanford, CA, pp. 278-292.

Marten et al. (1983) "Quality Prediction of Small Grain Forages by Near Infrared Reflectance Spectroscopy," *Crop Sci* 23:94-96.

Mathison et al. (1999) "Prediction of composition and ruminal degradability characteristics of barley straw by near infrared reflectance spectroscopy," *Can. J. Anim.* Sci. 79:519-523.

Mentink et al. (2006) "Utility of near-infrared reflectance spectroscopy to predict nutrient composition and in vitro digestibility of total mixed rations," *J. Dairy Sci.* 89:2320-2326.

Mould et al. (2005) "In vitro microbial inoculum: A review of its function and properties," *Anim. Feed Sci. Technol.* 123:31-50.

Norris et al. (1976) "Predicting forage quality by infrared reflectance spectroscopy," *J. Anim. Sci.* 43:889-897.

Nutrient Requirements for Dairy Cattle, 7th Revised Ed., Subcommittee on Dairy Cattle Nutrition, Committee on Animal Nutrition, National Research Council, Nat. Acad. Sci., Washington, DC.

Oba and Allen (2000) "Effects of brown midrib 3 mutation in corn silage on productivity of dairy cows fed two concentrations of dietary neutral detergent fiber: 1. Feeding behavior and nutrient utilization," *J. Dairy Sci.* 83(6):1333-1341.

Pell and Schofield, (1993) "Computerized monitoring of gas production to measure forage digestion in vitro," *J. Dairy Sci.* 76:1063-1073.

Rymer et al., (2005) "In vitro cumulative gas production techniques: History, methodological considerations and challenges," *Anim. Feed Sci. Technol.*123:9-30.

Shenk et al. (1979) "Analysis of forages by infrared reflectance," *J. Dairy Sci.* 62:807-812.

Shenk and Westerhaus (1991) "Population definition, sample selection, and calibration procedures for near infrared reflectance spectroscopy," *Crop Sci.* 31:469-474.

The Tilley and Terry Technique (1963) "A two-stage technique for the in vitro digestion of forage crops," *J. Br. Grassl. Soc.* 18:104-111.

Van Soest, Robertson & Lewis (1991) "Methods for Dietary Fiber, Neutral Detergent Fiber, and Nonstarch Polysaccharides in Relation to Animal Nutrition," *J. Dairy Sci.* 74:3583-3597.

Weiss, W.P. (1993) "Prevailing concepts in energy utilization by ruminants. Predicting energy values of feeds," *J. Dairy Sci.* 76:1802-1811.

Weiss, W. P. (1996) "Estimating Available Energy Content of Ruminant Feeds," *Proc. California Nutrition Conference*, 1-11, Fresno, California.

Williams (2000) "Cumulative gas production techniques for forage evaluation," in Forage Evaluation in Ruminant Nutrition, D. I. Givens, E. Owen, R. F. E. Axford, and H. M. Omed, eds. CABI Publishing, Wallingford, UK, pp. 189-213.

\* cited by examiner

METHOD FOR MEASURING FIBER DIGESTIBILITY

CROSS-REFERENCE TO RELATED APPLICATIONS

Priority is hereby claimed to provisional application Ser. No. 61/120,981, filed Dec. 9, 2008, and provisional application Ser. No. 61/037,165, filed Mar. 17, 2008, both of which are incorporated herein by reference.

FEDERAL FUNDING STATEMENT

This invention was made with United States government support awarded by the following agency: USDA/CSREES, 08-CRHR-0-6055. The United States government has certain rights in this invention.

FIELD OF THE INVENTION

The invention is directed to an in vitro method of measuring the digestibility of fiber (generally) in ruminants and the digestibility of neutral detergent fiber (specifically) in ruminants and constructing spectrophotometric calibration curves using the measured digestibility values.

BACKGROUND

The amount of energy a particular type of forage contributes to a ruminant diet is perhaps the single most important factor in predicting animal performance. Ruminant diets containing high-energy forages yield faster weight gains and greater milk production. However, accurately, precisely, and quickly measuring the energy content of forage currently is not possible.

In the past, empirical equations were used to predict forage energy content from a single analyte, such as acid detergent fiber (ADF) or crude protein (CP). While these empirical equations are generally accurate for large sample sizes, they yield imprecise results. In short, when examining a large database of forage energy contents predicted by an empirical equation, the empirical equation accurately predicts the average of the database. But the equation will not precisely predict the energy content of any single forage within the database. To be of practical value, a forage testing system must be able to determine (accurately and precisely) the energy content of any single forage.

One approach to measuring the energy content of forage is to measure the principal components in the forage that contribute energy, give each component a digestion coefficient, multiply each component by its respective digestion coefficient, and add the products together. (See Weiss, W. P. (1996) "Estimating Available Energy Content of Ruminant Feeds," *Proc. California Nutrition Conference*, 1-11, Fresno, Calif.) The disadvantage of this approach is that extensive laboratory measurements are needed. Four principal components need to be accurately and precisely measured: crude protein (CP), neutral detergent fiber (NDF), fat, and non-fiber carbohydrate (NFC). The digestion coefficients assigned to CP, fat, and NFC are well defined by research. (See Weiss, W. P. (1993) "Prevailing concepts in energy utilization by ruminants. Predicting energy values of feeds," *J. Dairy Sci.* 76:1802-1811.) However, the digestion coefficient for NDF (i.e., neutral detergent fiber digestibility, NDFD) is not well defined by research and is not easily determined in the lab.

NDFD is one of the more difficult assays to conduct in the laboratory. Most laboratories cannot conduct the assay because an in vitro NDFD laboratory procedure requires rumen fluid from a live cannulated cow. Conventionally, forage NDFD is measured via two methods: In the first method, forage samples are placed in small Dacron bags and inserted into the rumen of a cow via a ruminal cannula. The amount of NDF prior to ruminal incubation is compared to the amount of NDF remaining after ruminal incubation. NDFD is then calculated from the "before digestion" and "after digestion" NDF values to arrive at a value for NDF digestibility. This approach is generally referred to as the in situ method. While the in situ method is a viable method for estimating NDFD, not every lab can have a number of cannulated cows on hand to be used for this purpose. Also, there is large, uniform database of NDFD values determined via the in situ method.

In the second conventional method, an in vitro approach is taken. The basic process is as follows (see Goering & Van Soest (1970) "Forage Fiber Analyses (Apparatus, Reagents, Procedures, and Some Applications)," *Agric. Handbook No. 379*, pp 8-11, ARS-USDA, Washington, DC; see also Van Soest, Robertson & Lewis (1991) "Methods for Dietary Fiber, Neutral Detergent Fiber, and Nonstarch Polysaccharides in Relation to Animal Nutrition," *J. Dairy Sci.* 74:3583-3597): Feed is weighed into a glass flask. Buffers, macro- and micro-minerals are then added to the flask, along with rumen fluid extracted from a cow fit with a ruminal cannula. The forage, buffers, and rumen fluid are then incubated in a water bath in an anaerobic environment (carbon dioxide) at a cow's body temperature (102° F./39° C.) for 48 hours. After the 48 hours has passed, the flask containing the forage, buffers, and rumen fluid is removed from the water bath and the remaining solution is refluxed in neutral detergent solution for 1 hour. After refluxing, the remaining solution is filtered and the NDF that resisted digestion by rumen bacteria is retained on the filter. The digestible NDF values are then calculated by difference.

Only minor changes have been made to the in vitro NDFD assay since it was first put forth in 1970. As of 2001, the National Research Council recommended using a 48-hour incubation period. See "Nutrient Requirements for Dairy Cattle," 7th Revised Ed., Subcommittee on Dairy Cattle Nutrition, Committee on Animal Nutrition, National Research Council, Nat. Acad. Sci., Washington, DC.

The conventional in vitro NDFD assay thus suffers from two very distinct drawbacks: (1) it is slow: 48 hours; and (2) it is unacceptably imprecise because it uses rumen fluid that is not standardized. In short, the conventional in vitro assay requires using rumen fluid, which differs in its bacterial content and fiber digestion activity from cow-to-cow, and even from day-to-day within any given cow. In short, the enzyme activity of rumen fluid from one cow can (and does) differ significantly from the enzyme activity of rumen fluid from another cow. Thus, while the test yields accurate aggregated results (because the differences in rumen fluid enzyme activity cancel each other out over a large number of samples), it is not sufficiently precise to determine the NDFD of any specific forage sample.

Neutral detergent fiber (NDF) is that portion of a forage that is insoluble in a neutral detergent solution. Neutral detergent fiber digestibility (NDFD) is conventionally defined as the digestibility of neutral detergent fiber as determined by the difference in NDF in a forage before and after in vivo or in vitro digestion as described in earlier. The NDF value reflects the total content of the cell walls of the forage. This is in contrast to acid detergent fiber (ADF), which reflects the cell wall portions of the forage that are made up of cellulose and lignin. NDF comprises the ADF fraction, plus hemicellulose (which is insoluble in neutral detergent solution, but soluble in acid detergent solution). Neutral detergent fiber values are important in ration formulation because they inversely reflect the amount of forage the animal can consume. As NDF percentage increases, dry matter intake generally decreases. In short, cows will eat more forage if the forage is low in NDF. NDF is the thus an accurate indicator of how much forage (on average) a herd will eat. For example, a high-producing dairy cow can eat about 1.1% of her body weight in NDF per day. If a grass forage has 50% NDF, a 1,300-pound cow will eat (on average) about 29 pounds of forage dry matter per day (1300×0.011/0.50=28.6). In contrast, that same 1,300-pound cow will eat (on average) about 36 pounds of forage dry matter per day of a forage containing only 40% NDF (1300×0.011/0.40=35.75). Because the cost of feed and the ultimate productivity of the herd are critical economic variables, the ability to measure NDFD accurately and precisely for any given type of forage is thus critical to maximizing profits from the on-going operations of dairy and meat herds. Likewise, the ability to measure NDFD is very important for commercial breeders of forage plants. Measuring NDFD of a forage or other biomass material is also important in the production of ethanol and other chemicals by enzymatic degradation and fermentation of biomass.

Norris et al. (1976) "Predicting forage quality by infrared reflectance spectroscopy," *J. Anim. Sci.* 43:889-897 first recognized near-infrared reflectance spectroscopy (NIRS) was capable of predicting forage quality parameters, such as in vitro dry matter disappearance. Shenk et al. (1979) "Analysis of forages by infrared reflectance," *J. Dairy Sci.* 62:807-812 acknowledged that NIRS had utility for commercial forage testing laboratories because NIRS instruments could offer rapid nutrient prediction. Shenk et al. (1979) also mentioned that two keys to success for NIRS prediction were: (1) the calibration samples must be representative of the population to be predicted; and (2) the reference laboratory data must be accurate. Abrams et al. (1987) "Determination of forage quality by near-infrared reflectance spectroscopy-efficacy of broad-based calibration equations," *J. Dairy Sci.* 70:806-813 partially answered Shenk et al.'s (1979) first concern by determining a calibration set of at least 100 samples was necessary to approach the smaller error statistics of sample sets in excess of 400 forages.

The second key has been addressed by a number of studies, where acceptable reference technique accuracy and precision, as indicated by successful NIRS predictions, has been achieved for forage quality parameters such as NDF, in situ protein fractions, and in vitro dry matter disappearance. See Buxton and Mertens (1991) "Errors in forage-quality data predicted by near infrared reflectance spectroscopy," *Crop Sci.* 31:212-218; Hoffman et al. (1999) "Prediction of laboratory and in situ protein fractions in legume and grass species using near-infrared reflectance spectroscopy," *J. Dairy Sci.* 82:764-770; and Mentink et al. (2006) "Utility of near-infrared reflectance spectroscopy to predict nutrient composition and in vitro digestibility of total mixed rations," *J. Dairy Sci.* 89:2320-2326. However, two attempts to calibrate NIRS to in vitro NDF digestibility data have failed: Andres et al. (2005) "Prediction of aspects of neutral detergent fiber digestion of forages by chemical composition and near-infrared reflectance spectroscopy," *Aus. J. Agric. Res.* 56: 187-193; and Mentink et al., (2006) "Utility of near-infrared reflectance spectroscopy to predict nutrient composition and in vitro digestibility of total mixed rations," *J. Dairy Sci.* 89:2320-2326. In their 2006 paper, Mentink et al. attributed the failure to a lack of precision with the in vitro ruminal digestion technique.

Thus, while the NDFD content of forage can be roughly predicted using near infrared spectroscopy (NIRS), there is a considerable loss of precision. See Combs (1998) "Using NIR to Evaluate Forage Quality," *Proc. of the 4-State Forage Feeding and Management Conference, University of Wisconsin-Extension,* 129-135, Madison, Wis. Thus, current NIRS-based methods for predicting NDFD are less accurate and precise that the conventional in vivo method described by Goering & Van Soest, supra.

Neutral detergent fiber digestibility is an important parameter in modeling ruminant dietary digestion because the NDF fraction can be 30% or greater of dietary dry matter and digestibility can range from 30% to greater than 70% (Goeser and Combs, unpublished data). Thus, there remains a long-felt and unmet need for a method that determines fiber digestibility in general, and neutral detergent fiber digestibility in particular that is fast, accurate, and precise.

SUMMARY OF THE INVENTION

The preferred version of the invention is directed to a method of measuring fiber digestion in ruminants. The method comprises harvesting rumen fluid from at least one ruminant animal and combining the rumen fluid with a primer composition comprising a carbohydrate. The rumen fluid and carbohydrate are then incubated until a pre-determined endpoint is achieved. In the preferred version, the rumen fluid and carbohydrate are incubated in a sealed container until a pre-determined pressure is achieved within the sealed container—the pre-determined pressure being the endpoint. The rumen fluid is now referred to as primed rumen fluid. A plant matter sample, such as forage, is then digested with the primed rumen fluid of step. The fiber content of the digested plant matter sample is then measured and compared to the fiber content of a non-digested sample.

In a preferred version of the invention, the primer composition comprises cellulose. It is more preferred that the primer composition comprises cellulose and one or more additional ingredients selected from the group consisting of urea, starch, cellobiose, or combinations thereof. It is most preferred that the primer composition comprises all of cellulose, urea, starch, and cellobiose, and that these ingredients are disposed in a buffered reducing solution. The reducing solution preferably comprises an aqueous solution of cysteine hydrochloride, sodium sulfide, and sodium hydroxide.

It is preferred that the method be used to measure the neutral detergent fiber content of the digested plant matter sample. Alternatively, any other fiber faction of the sample, such as acid detergent fiber, may additionally (or alternatively) be measured.

Another version of the invention is directed to a method of calibrating a spectrophotometer. The method comprises harvesting rumen fluid from at least one ruminant animal and combining the rumen fluid with a primer composition comprising a carbohydrate. The rumen fluid and carbohydrate are then incubated until a pre-determined endpoint is achieved, thereby yielding primed rumen fluid. A plant matter sample is then digested with the rumen fluid to yield a digested sample. The fiber content of the digested sample is measured and recorded. The absorbance or reflectance of the digested sample is also measured and recorded using a spectrophotometer. Then the spectrophotometer is calibrated by correlating the measured fiber content with the measured absorbance or reflectance. The data can also be used to calibrate other spectrophotometers of the same or similar design. In this version of the invention, it is preferred that the absorbance of the digested sample is measured using a near-infrared spectrophotometer.

Another version of the invention is directed to a method of constructing a standard curve, and the standard curves produced using the method. The method comprises incubating rumen fluid from at least one ruminant animal and a carbohydrate until a pre-determined endpoint is achieved, thereby yielding primed rumen fluid. A plant matter sample is then digested with the rumen fluid to yield a digested sample. The fiber content of the digested sample is measured and recorded. The absorbance or reflectance of the digested sample is also measured and recorded using a spectrophotometer. These steps are then repeated for one or more additional plant matter samples. A standard curve is constructed by correlating the measured fiber content of each sample with its corresponding measured absorbance or reflectance. The resulting standard curve is useful for calibrating spectrophotometers and for predicting fiber content in forage samples via spectrophotometric analysis in general, and NIRS analysis in particular. The standard curve so produced are within the scope of the present invention.

DETAILED DESCRIPTION OF THE INVENTION

The invention is directed to a method for precisely estimating ruminal fiber digestion in an in vitro assay. The method is capable of precision necessary to estimate NDF digestion kinetics. The values generated by the assay can also be used to generate standard calibration curves for NIRS-based measurements of fiber digestibility in general and neutral detergent fiber digestibility (NDFD) in particular.

The discussion which follows is limited to a discussion of determining NDFD, which is the preferred version of the invention. This is for brevity only. The invention can also be used to determine the digestibility of other fiber fractions, such as acid detergent fiber. The approach taken in the preferred version of the present invention is purposefully designed to remove or limit the variables in the conventional Goering & Van Soest in vivo method of determining NDFD. One or more of the following steps are utilized in the invention: In a preferred version, the invention uses a standardized feed mixture that is fed to the cows whose rumen fluid is used in the present invention. The rumen fluid collected from the cows is then pre-treated to allow the microbial flora present in the rumen fluid to balance to a standard activity. It is the microbial flora present in the rumen fluid which digests the NDF present in the forage consumed by a ruminant. In the preferred version of the invention, it is the rate of digestion that is measured, rather than the amount of NDF digested after a specific time period. Lastly, in the preferred version of the invention the forage sample is subjected to in vitro digestion while contained within a porous filter bag wherein the porosity of the bag is no greater than about 50 µm.

Figure 1:
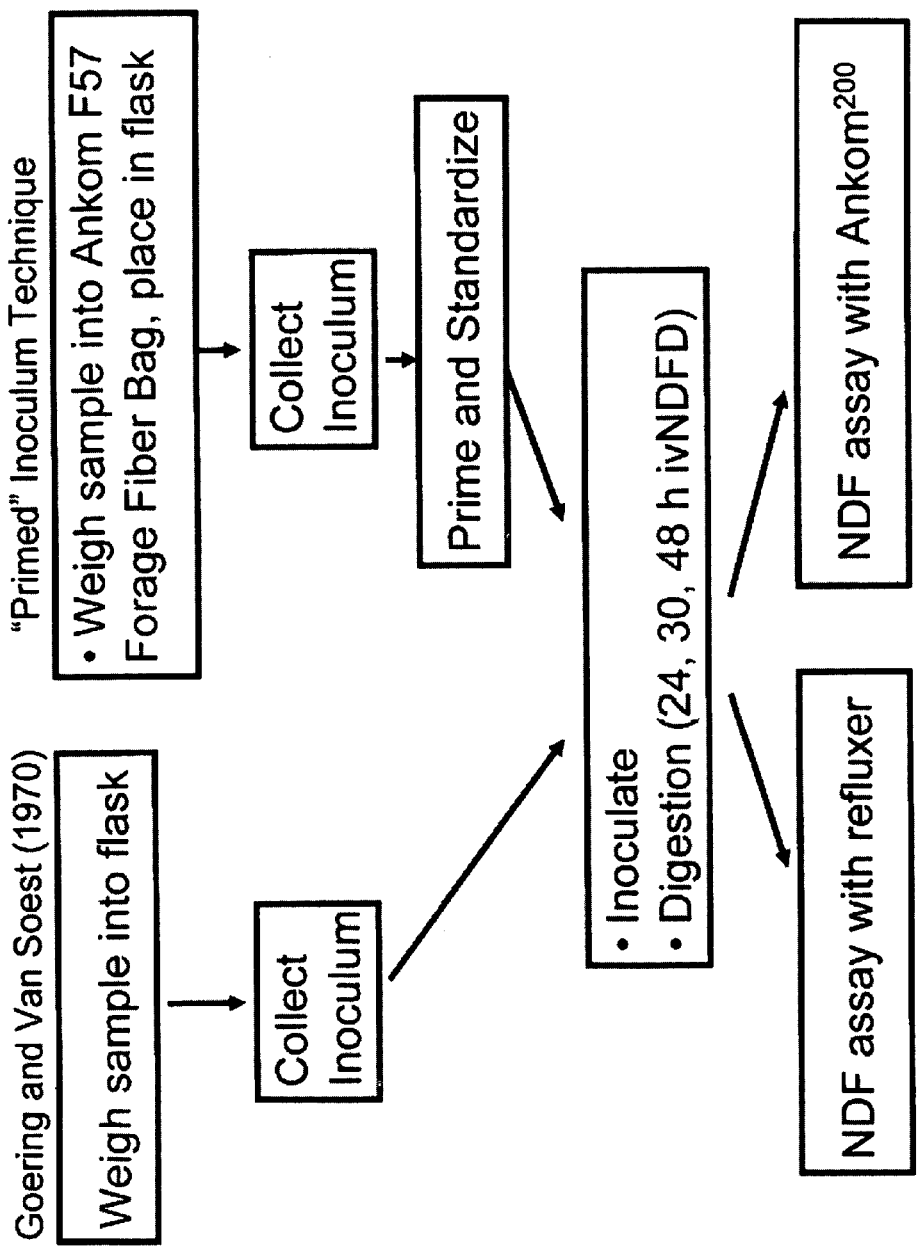
FIG. 1 is a flow chart depicting the preferred version of the present invention (right-hand side of figure) compared to the conventional Goering & Van Soest NDFD protocol.

The preferred version of the invention is illustrated schematically in FIG. 1, along with a comparison to the conventional Goering & Van Soest in situ/in vitro method. The process of the present invention is presented in the right-hand side of FIG. 1, under the title "Primed Inoculum Technique." As indicated on the right-hand side of FIG. 1, the forage sample is weighed into a filter bag, preferably an "ANKOM"-brand model F57 bag. The inoculum of rumen fluid is then collected, primed and standardized (this step is described in full below), and the filter bag with the forage sample within it is then inoculated with the inoculum and allowed to digest for a pre-determined time period. Most preferably the time period for digestion is 18 to 48 hours. After digestion, the filter bags are rinsed in cold distilled water (not shown in FIG. 1) and analyzed for neutral detergent fiber using, for example, and "ANKOM"-brand fiber analyzer. Neutral detergent fiber digestibility is then calculated as (1−neutral detergent residue remaining after a specific time÷neutral detergent fiber content of sample)×100.

In contrast to the present invention, in the Goering & Van Soest method, the sample is digested in a conventional glass flask and the rumen fluid for use in the digestion is neither primed nor standardized prior to the digestion. Rather, the conventional Goering & Van Soest method entails beginning the digestion as quickly as possible after the rumen fluid is taken from the cannulated cow. There is, however, a variable lag time between when the sample is contacted with the rumen fluid and when significant digestion of the sample actually begins to occur. It is primarily this variable lag time in the conventional approach that requires the test to be run over a 48-hour period. If the digestion period is truncated in the conventional method, the variable time lag before digestion starts in earnest renders the results irreproducible. In the present invention, the raw rumen fluid is treated (i.e., "primed") and standardized to a specific activity prior to the start of the digestion. This priming process standardizes the lag time between when the sample is immersed in the rumen fluid and when digestion reaches its maximum rate. The process of priming the rumen minimizes the variability in the lag time period itself. So in the present invention, the lag time prior to maximum digestion rate is shortened and the lag time variability is narrowed.

The present invention addresses a very specific need in the industry, namely, how to measure NDFD accurately and precisely, not in the average, but for a specific forage sample. Until now, run-to-run variance due to the inconsistent nature of rumen fluid inoculum confounds comparisons of forage in vitro NDF digestibility (NDFD) values gathered in different repetitions or in different laboratories. In short, the results obtained in one lab or in one batch of measurements for any given forage sample vary so significantly from the results in other batches and/or other labs, that direct head-to-head comparisons of specific NDFD values are not possible.

In the present invention, rather than harvesting the rumen fluid and running the NDFD test as quickly as possible (as is done in the conventional Goering & Van Soest method), the rumen fluid is harvested, primed and allowed to reach a pre-determined activity level before inoculating a forage. In this fashion, the repeatability of the assay is markedly improved.

While not being limited to a specific mechanism, it is believed that the rumen microflora undergo considerable stress during the inoculum collection process. Therefore, using the rumen fluid immediately simply subjects the microflora to further stress. In the present invention, the microflora in the rumen fluid are given an opportunity to recover and stabilize. They are then "fed" a priming composition. Gas production by the microflora in response to the added primer is then used as a means to measure the activity of the inoculum. Once the inoculum has reached a suitable activity level, the digestion assay is begun.

In the preferred version of the invention, the rumen fluid is combined with a reducing solution and primed with a primer composition comprising cellulose. The rumen fluid mixture is then allowed to incubate in a sealed vessel until a pre-determined pressure is achieved. Once the pre-determined pressure is achieved, the rumen fluid is used to digest forage samples. The NDF value of the digested forage samples is then determined and compared to the NDF value of undigested forage samples to arrive at percentage value for neutral detergent fiber digestibility (NDFD).

Priming the Rumen Fluid:

A critical step in the present invention is to prime and standardize the activity of the rumen fluid that is used in the assay. This is accomplished by incubating the raw rumen fluid collected from a cow under reducing and buffered conditions and in the presence of a primer composition. The raw rumen fluid is collected into a pre-warmed flask (about 39° C., the internal temperature of the rumen). Preferably the raw rumen fluid is collected from two or more cows. This reduces cow-to-cow variability in the raw rumen fluid. While maintaining the temperature at 39° C., the raw rumen fluid is strained into a $CO_2$-purged flask to remove solids. This can be done with filter paper or through layers of common cheesecloth.

At the same time or prior to the collection of raw rumen fluid, a series of flasks are assembled containing a primer composition disposed within a buffered reducing solution. The reducing solution preferably comprises an aqueous solution of cysteine hydrochloride, sodium sulfide, and sodium hydroxide. (The sodium sulfide can be anhydrous, $Na_2S$, or hydrated, $Na_2S.9H_2O$. The hydrate is preferred.) The preferred reducing solution contains about 1.875 g cysteine HCl, about 1.875 g $Na_2S.9H_2O$, and about 12 ml 1N NaOH disposed in 290 ml distilled $H_2O$. The buffer solution comprises an aqueous solution of sodium bicarbonate and ammonium bicarbonate. The preferred buffer solution contains 620 g $NaHCO_3$ and 72 g $NH_4HCO_3$ in 18 L distilled $H_2O$. Where rumen fluid is used in 250 ml batches, it is preferred that 50 ml of reducing solution and 250 ml of buffer solution be combined with each 250 ml batch of rumen fluid. Concentrations of the individual reagents within the reducing solution above and below the stated preferred version are explicitly within the scope of the present invention, as are different ratios of rumen fluid to buffered reducing solution.

The primer composition comprises, at minimum cellulose, preferably ground crystalline cellulose, that is combined with the reducing solution mixture prior to adding the rumen fluid. For the rumen fluid/reducing solution described in the previous paragraph (250 ml rumen fluid in 300 ml of buffered reducing solution), about 0.1 to about 1 g of cellulose would be added to prime the rumen fluid/reducing solution mixture. More preferably, from about 0.1 to about 0.5 g of cellulose would be added to prime the rumen fluid/buffered reducing solution mixture. Amounts of cellulose above and below these stated values are explicitly within the scope of the invention.

While cellulose alone can be used to prime the rumen fluid, it is preferred that the primer composition contain additional ingredients. Thus, in the preferred embodiment of the invention the primer composition comprises, in addition to cellulose, urea, starch, and/or cellobiose. The primer composition may comprise cellulose plus any combination of one or more of the three additional ingredients. The ingredients are admixed together to yield the primer composition. The ingredients may be in the primer composition in equal or unequal portions. In the most preferred version of the invention, the primer composition comprises all of cellulose, urea, starch, and cellobiose. The most preferred primer composition comprises (on a dry matter basis) about 40% cellulose, about 20% urea, about 20% starch, and about 20% cellobiose. Concentrations above and below these stated values are explicitly within the scope of the invention.

To ensure the all sources of run-to-run variability are kept to a minimum, it is preferred that a series of flasks containing a combination of buffered reducing solution and the primer are made up in advance of harvesting the raw rumen fluid. That way, once the rumen fluid is harvested and filtered, the rumen fluid aliquots can be added directly into flasks that already contain a combination of the primer and the buffered reducing solution. The mixture of primer and buffered reducing solution can be made in advance, in which case it should be stored in a sealed container under carbon dioxide until it is combined with the rumen fluid.

The rumen fluid is then distributed in 50 ml aliquots to the series of flasks containing the primer and buffered reducing solution until each flask contains a pre-determined, final amount of rumen fluid. In the case of the examples presented below, the raw rumen fluid was distributed, 50 ml at a time, into six (6) 1 L sidearm Erlenmeyer flasks in series until a final volume of 250 ml of rumen fluid was added to each flask. That is, a 50 ml aliquot of rumen fluid is deposited into each flask prior to adding the next round of 50 ml aliquots to each flask. This approach reduces rumen fluid variability in the event that the flora within the rumen fluid is not equally distributed within the bulk volume of raw rumen fluid. In this fashion, each flask receives similar starting bacterial concentration. The flasks containing the rumen fluid, primer, and reducing solution are then purged with $CO_2$, sealed, and placed in a shaking incubator at about 39° C. until the sealed flasks reach a pre-determine pressure, preferably about 20 inches of water (~37.4 torr; ~4.98 MPa). When using 1 L flasks, this typically takes about 2 hours. The pressure value is a pre-determined value that serves as an endpoint to indicate that the rumen fluid has been sufficiently primed. The user evaluates it empirically, and may adjust accordingly either to lengthen or shorten the overall time course of the assay. Thus, pressure values above or below the preferred 20 inches of water are explicitly within the scope of the invention. Other endpoints may also be used, such as pH of the rumen fluid, or an endpoint based on the consumption of the added cellulose.

When the pressure has reached the desired level in the series of flasks, the rumen fluid is considered "primed." The primed rumen fluid from the series of flasks is then combined into a single flask (which has been purged of oxygen) and used to inoculate the forage samples. Combining the primed rumen fluid again limits the batch-to-batch variability of the primed rumen fluid when it is used in the digestion assay.

Preparing the Forage Samples for Digestion:

To prepare the forage samples for testing, they are ground to approximately 1 mm particle size. A pre-determined amount of ground forage is then weighed into a filter bag. In the examples, a 0.5 g sample size was chosen. This was purely arbitrary and any size sample may be used, as the tester desires. The filter bag is then sealed. As noted earlier, it is preferred that the filter bag have a porosity of 50 μm or less. This is to ensure that all of the insoluble neutral detergent fiber is retained within the filter bag, thereby minimizing gravimetric losses. ANKOM-brand "F57" filter bags are preferred (available commercially from Ankom Technology, Macedon, N.Y.). This particular type of filter bag has a porosity of about 25 μm. Other bag types produced by Ankom Technology ("R510," "R1020," "XT4,"etc.) may also be used. Ankom's "R510" and "R1020" model bags have a porosity of 50 μm; the "XT4" model bags have a porosity of 1 μm. Suitable filter bags for use in the present invention can also be obtained from several other commercial makers and suppliers, including 3M, GAF, Grainger, Parker, McMaster-Carr, U.S. Filter, and many others.

Once the filter bags are filed and sealed, they remain sealed for the entire procedure. Prior to beginning each run, the sample bags to be tested are placed in the bottom of a suitable vessel (e.g., individual 125 ml Erlenmeyer flasks), and secured in a shaking water bath set at 39° C.

Four solutions used in the assay may be assembled in bulk, in advance. "Solution A" and "Solution B" are used to fabricate the "in vitro media solution." The solutions are:

Solution A (for 1800 samples):
18.0 L distilled $H_2O$
102.6 g $Na_2HPO_4$
111.6 g $KH_2PO_4$
10.5 g $MgSO_4.7H_2O$
Solution B (for 25,000 samples):
13.2 g $CaCl_2.2H_2O$
10.0 g $MnCl_2.4H_2O$
1.0 g $CoCl_2.6H_2O$
8.0 g $FeCl_3.6H_2O$
Brought to 100 ml with distilled $H_2O$
In vitro media solution (for 150 samples):
3 L distilled $H_2O$
1500 ml Solution A
0.6 ml Solution B
12.0 g trypticase peptone
6.0 ml resazurin indicator For 0.5 g forage samples, it is preferred that about 30 ml of in vitro media solution be added to each forage sample. The flasks containing the samples are then purged of oxygen (e.g., by using a conventional manifold to pass $CO_2$ or some other purging gas through the flasks) and the flask are sealed. The sealed flasks are held at 39° C. overnight (i.e., about 8 to 12 hours).

At this point, the treated forage samples are ready to being the digestion assay.

The Digestion Assay:

Again using a 0.5 forage sample size as an illustration, about 22 ml of the primed rumen fluid (prepared as described above) is added to each flask containing a treated forage sample. Each flask is then purged of oxygen, sealed, and maintained at about 39° C. The time when the primed rumen fluid is added to the treated forage sample should be noted. About 6 hours after the digestion has begun, the flasks should be opened briefly and the filter bags deflated of accumulated gases. This can be done with a glass rod or a rubber policeman or any other suitable tool. Deflating the bags should be done gently (so as not to pierce the filter bags) but quickly so as to minimize contact of the samples with oxygen. The process should be repeated, preferably at three additional time points—at 24 h, 30 hr, and 48 hr. Deflating the filter bags ensures contact of the forage sample with the digestion medium.

After the digestion is complete, the filter bags are rinsed three times with cold distilled water until the effluent runs clear. The filter bags are then ready to be analyzed for their NDF content. If several days will pass before the NDF analysis is performed, the filter bags should be dried at about 60° C. overnight. NDF is then determined using any means now known or developed in the future for measuring NDF.

Measuring NDF in the Digested Samples:

Determination of NDF in the digested samples is accomplished by conventional and well-established means. NDF determination can be done manually (less preferred because it is laborious) or automatically using commercially available automation equipment (more preferred for ease, speed, and reproducibility). The discussion that follows is limited to a description of a well-known automated fiber-measuring machine fabricated by Ankom Technology. Note that while the process described herein is given in relation to the "ANKOM"-brand fiber analyzer, the process is essentially identical when performed manually.

The "ANKOM"-brand fiber analyzer provides an automated, easy to use method for determining acid detergent fiber, neutral detergent fiber, and crude fiber values in feeds and forages. In this particular device, up to 24 samples prepared and digested as described above can be tested for NDF content simultaneously. The filter bags, with sample, are placed in a bag suspender and inserted into a fiber analyzer vessel. The user closes the vessel lid, follows screen prompts to program the operation desired (NDF in this instance) and pushes the start button. The fiber analyzer automatically inserts the needed detergent solution, solubilizes the nonfiber components of the samples, and filters the samples. Soluble cell contents are removed while the fiber component of each sample is retained in the filter bag. The detergent step is followed by a series of automatic rinsing steps. The samples are then removed, dried, reweighed and fiber values determined.

An illustrative protocol for determining NDF using an automated NDF analyzer is as follows:

Apparatus:

1. Analytical Balance—capable of weighing down to 0.1 mg.

2. Oven—capable of maintaining a temperature of 102±2° C.

3. An automatic digestion instrument—capable of performing the digestion at 100±0.5° C. and maintaining a pressure of 10-25 psi. The instrument must also be capable of creating a similar flow around each sample to ensure uniformity of extraction. (In the examples, an $ANKOM^{2000}$—brand device with 65 rpm agitation was used.)

4. Filter bags with forage samples digested as described herein.

5. Heat sealer—sufficient for sealing the filter bags.

6. Desiccator pouch—a collapsible sealable pouch with desiccant inside that enables the removal of air from around the filter bags (e.g., MoistureStop-brand weigh pouch, ANKOM Technology).

7. Marking pen—solvent resistant (to label the filter bags).

Reagents:

1. Neutral Detergent Solution—Add 30.0 g sodium lauryl sulfate, USP; 18.61 g ethylenediaminetetraacetic disodium salt, dihydrate; 6.81 g sodium tetraborate decahydrate; 4.56 g sodium phosphate dibasic, anhydrous; and 10.0 ml triethylene glycol, in 1 L distilled $H_2O$, pH 6.9 to 7.1. Agitate and heat to aid dissolution.

2. Alpha-amylase—Heat-stable bacterial alpha-amylase: activity 17,400 liquefon units/ml.

3. Sodium sulfite—$Na_2SO_3$, anhydrous.

Procedure:

1. Use the solvent-resistant marker to label the filter bags. Weigh filter bag ($W_1$) and zero balance.

2. Place 0.45-0.55 g of the forage sample directly into the filter bag and weigh ($W_2$).

3. Using a heat sealer, completely seal the upper edge of the filter bag within 4 mm of the top.

4. Weigh one blank bag and include it in the NDF run to determine the blank bag correction ($C_1$). At this point, the bags are subjected to the rumen fluid digestion described hereinabove.

5. After the rumen fluid digestion, extract samples by placing the rumen fluid-digested samples into a container with a top. Pour enough acetone into the container to cover bags and secure the top. Shake the container 10 times and allow the filter bags to soak for 10 minutes. Repeat with fresh acetone. Pour out the acetone and place the bags on a wire screen to air-dry.

6. Place the filter bags into the bag suspender and insert the bag suspender with the filter bags attached into the fiber analyzer vessel.

7. Follow the manufacturer's directions for programming and starting the NDF analysis. In the ANKOM$^{2000}$ device, NDF analysis is pre-programmed into the device. A user simply selects "NDF," closes the lids, and presses the "start" button. After the neutral digestion solution has been automatically inserted into the vessel and agitation begins, manually add 20 g of $Na_2SO_3$ and 4.0 mL of alpha-amylase.

8. Attach amylase dispenser to "Port B" of the Ankom device and fill the dispenser with 8.0 ml. of alpha-amylase diluted to a volume of 350 mL. The fiber analyzer device will automatically add this amylase solution to the first and second rinse cycles.

9. When the NDF extraction and rinsing process is complete, open the lid and remove the samples. Gently press out excess water from bags. Place bags in a 250 mL beaker and add enough acetone to cover bags and soak for 3-5 min.

10. Remove the filter bags from the acetone and place on a wire screen to air-dry. After the filter bags are air-dried, completely dry them in an oven at 102±2° C. (This drying step takes approximately 2 to 4 hours).

11. Remove bags from oven, place directly into a collapsible desiccant pouch and flatten to remove air. Cool to ambient temperature and weigh the filter bags ($W_3$).

Calculations:

$$\% \ NDF \ \text{(as-received basis)} = \frac{(W_3 - (W_1 \times C_1))}{W_2} \times 100$$

wherein: $W_1$=bag tare weight;

$W_2$=bag+sample starting weight;

$W_3$=dried weight of bag with fiber after extraction process; and $C_1$=Blank bag correction (final oven-dried weight divided by the original blank bag weight).

The process is performed in parallel with undigested samples and rumen fluid digested samples to arrive at a value for NDFD. See the examples for the detailed calculation.

Measuring ADF in the Digested Samples:

As noted above, the present invention is not limited to measuring NDFD. The digestibility of other fiber fractions, such as ADFD, may also be measured. The procedure is similar to that given above for NDF determination, with the exception that an acidic detergent solution is used in place of a neutral detergent solution. The conventional acidic detergent solution comprises 20 g of cetyl trimethylammonium bromide (CTAB) dissolved in 1 L of 1.00 N sulfuric acid.

EXAMPLES

The following examples are presented herein solely to provide a more complete description of the invention disclosed herein. The examples do not limit the scope of the invention in any fashion.

Example 1

Standard Protocol:

This example presents the basic materials, methods, and calculations to carry out an exemplary preferred version of the present invention. The starting time given (3:00 pm) is for convenience only and is provided solely to illustrate how best to coordinate the timing of the various steps of the process.

Materials Needed:

Solutions Equipment:

(2) 18 L carboys for macro-mineral and buffer (1) 250 ml flask for micro-mineral (1) 125 ml flask for resazurin indicator (1) 1 L flask for 1N NaOH Rumen in Vitro System:

Two shaking water baths set to 39° C., with lids, racks/clamps to secure flasks

Two $CO_2$ tanks with appropriate glass gas manifolds, one in warm room and one with water baths Timesheets/water bath maps (to describe where flasks are located)

Approximately (250) 125 ml Erlenmeyer flasks

5 rubber stoppers (2-hole) w/glass tubes for connecting to rubber hose to connect to gas manifold and rubber policemen with 4 mm cuts (vertical)

pH meter
Alfalfa standard sample
Inoculation Equipment:
Brinkman auto-dispenser, attached rubber hose and pipette tip for precise delivery of fluids
(1) 4 L Erlenmeyer side-arm flask in which the Brinkman fits, with attached rubber hose and spring clamp
Aluminum Foil
Warm Room Inoculum Preparation Equipment:
Traceable Pressure meter (e.g., VWR-brand, VWR Labshop, Batavia, Ill.)
(6) 1 L Erlenmeyer side-arm flasks, with attached rubber hose and spring clamps
(6) #7 rubber stoppers
(1) 6 L Erlenmeyer flask
(1) 300 ml Erlenmeyer flask for reducing solution
(1) 2 L Erlenmeyer flask
Cheesecloth
Large and small funnel
Various glassware for distributing fluids (e.g., IL graduated cylinder)
Rumen Fluid Collection Equipment:
Stainless steel barrel pump for collecting fluid, with attached strainer to prevent pumping of large particles
(2) glass-lined thermos's
5 gallon bucket to carry equipment
Methodology:
Approximately 0.5 g dried, ground (1 mm) forage sample is weighed into an "ANKOM"-brand F57 fiber bag and heat sealed; the bags remain sealed for the entire procedure. The day prior to inoculation, at, for example, 3:00 p.m., sample bags are placed in the bottom of 125 ml Erlenmeyer flasks that are secured in a shaking water bath, set at 39° C. The following solutions and primer are prepared in advance, preferably on a large-scale basis:

Solution A (1800 samples):
18.0 L distilled $H_2O$
102.6 g $Na_2HPO_4$
111.6 g $KH_2PO_4$
10.5 g $MgSO_4.7H_2O$ Solution B (25,000 samples):
13.2 g $CaCl_2. 2H_2O$
10.0 g $MnCl_2.4H_2O$
1.0 g $CoCl_2.6H_2O$
8.0 g $FeCl_3.6H_2O$
Brought to 100 ml with distilled $H_2O$ Buffer solution (1800 samples):
18.0 L distilled $H_2O$
630 g $NaHCO_3$
72.0 g $NH_3HCO_3$ Primer (Dry Matter (DM) Basis):
40% Cellulose
20% Urea
20% Starch
20% Cellobiose The following solutions should be prepared the day prior to inoculation:
In vitro media solution (150 samples):
3000 ml distilled $H_2O$
1500 ml Solution A
12.0 g trypticase peptone
0.6 ml Solution B
6.0 ml resazurin indicator Reducing solution (150 samples):
1.875 g Cysteine HCl
1.875 g $Na_2S.9H_2O$
290 ml distilled $H_2O$
12 ml 1N NaOH Add 30 ml of in vitro media solution to the flasks to each flask containing bagged sample. All flasks should then be sealed with a rubber stopper, which is attached to a manifold for continuous $CO_2$ gassing of the flasks. The flasks, containing media and sample should be briefly purged with $CO_2$ (5-15 min) and warmed overnight. Add 250 ml buffer solution to each of (6) 1 L Erlenmeyer side-arm flasks, purge with $CO_2$, and seal with rubber stopper and clamps. Place the 1 L flasks in warm room overnight. The following day at approximately 5:30 a.m., the flasks should be purged continuously with $CO_2$, while rumen fluid is being collected. Primer (0.3125 g per flask) and 50 ml of reducing solution are then added to each of the six 1000 ml sidearm Erlenmeyer flasks. The flasks are then held under $CO_2$ until combined with rumen fluid.

At 6:00 a.m. (prior to the cows being fed), approximately 1 L of rumen fluid should be collected into pre-warmed, glass-lined thermos flasks from each of two ruminally cannulated lactating cows (Holsteins were used in this example) on an 95% forage diet. In the warm room (39° C.), strain fluid through two layers of cheesecloth and then pool in a 2 L Erlenmeyer flask, held under $CO_2$. Purge the 2 L flask with $CO_2$, insert rubber hose, and seal. Add 50 ml allotments of rumen fluid in a rotating sequence to each of the 1 L sidearm Erlenmeyer flasks using rubber hose (to draw fluid from bottom of flask) and a 60 ml catheter tip syringe, until 250 ml rumen fluid has been added to each flask. The 50 ml allotments should be added in rotating pattern, so that each flask receives similar bacteria concentration. It is important to add the 50 ml aliquots one at a time and sequentially to the flasks, rather than filling a first flask completely to 250 ml and then moving to the next flask.

Set the (6) 1 L sidearm flasks in a shaking incubator, within the warm room, and allow the flasks to reach a pressure of 20 inches of water. It typically takes approximately 2 h for this pressure to be achieved. After reaching a pressure of 20 inches of water, the fluid should be recombined in the 4 L side-arm Erlenmeyer flask wrapped in aluminum foil (attached to $CO_2$ while combining) and used to inoculate the flasks containing the forage samples. Add 22 ml of rumen fluid inoculum solution to each sample flask through the glass tube by removing the rubber policeman and pumping. At approximately 3:00 p.m. on the day of inoculation and each following day, deflate the bags by turning $CO_2$ pressure up slightly, opening each flask, and manually deflating the Ankom bag using a rubber policeman or similar utensil. This should be done as quickly as possible to minimize sample exposure to oxygen. (As a practical matter, the process is very simple after a little practice and takes only 1 or 2 seconds.) Following deflating, return the $CO_2$ flow rate to a "trickle" or until a barely audible flow of gas can be heard when using a needle valve regulator.

Preferably, samples are removed at three time points: 24, 30, and 48, hours after inoculation for kinetic analysis. An empty flask should replace each removed flask to maintain gas flow throughout system. Rinsing the bags with cold, distilled water until effluent is clear terminates fermentation. If several days will pass before samples will be analyzed for NDF, the bags should be dried in a 60° C. oven overnight. Sample residue NDF is then determined using laboratory forage NDF reference procedures, with a single alfalfa standard included in each Ankom NDF run for quality control within the NDF assay. It is recommended to duplicate samples in each in vitro run for each sample/time point combination. Preferably, a standard alfalfa sample is included with each run for quality control of the NDFD assay.

Calculations:

NDF (% of DM)=[((bag wt.+residue)−(bag wt.·bag correction factor))/((bag wt.+sample)− (bag wt.)]·100

NDFD (% of NDF)= [(1−NDF residue$_{following\ digestion}$)/ (NDF$_{0\ h\ sample}$)]·100

Kinetic Analysis (single-compartment exponential model using R-statistical program):

NDFD<$I${Time>lag}*Extent*(1−exp($e^{-k}$(Time−lag)))

Use starting estimates of lag=10, k=0.05, extent=45

Figure 2A:
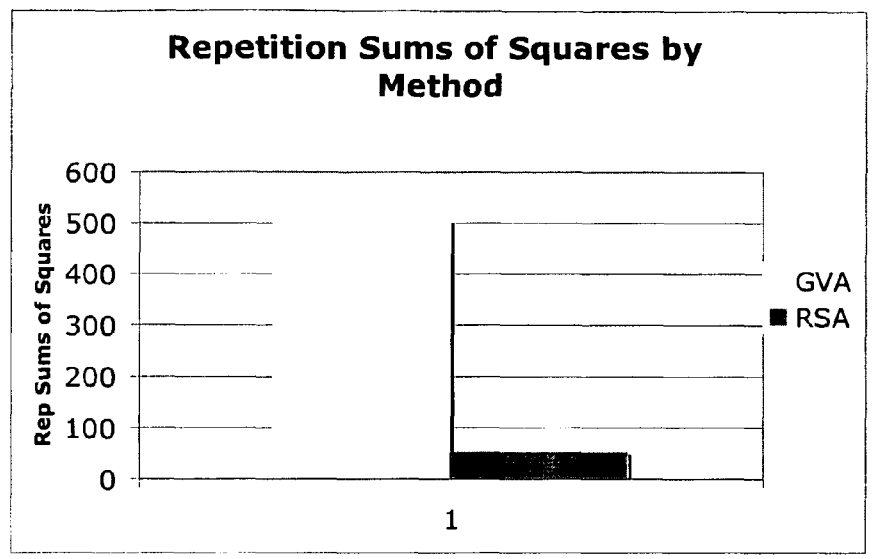
FIGS. 2A and 2B are comparisons of run to run error with the present invention and a Goering and Van Soest NDFD protocol
Figure 2B:
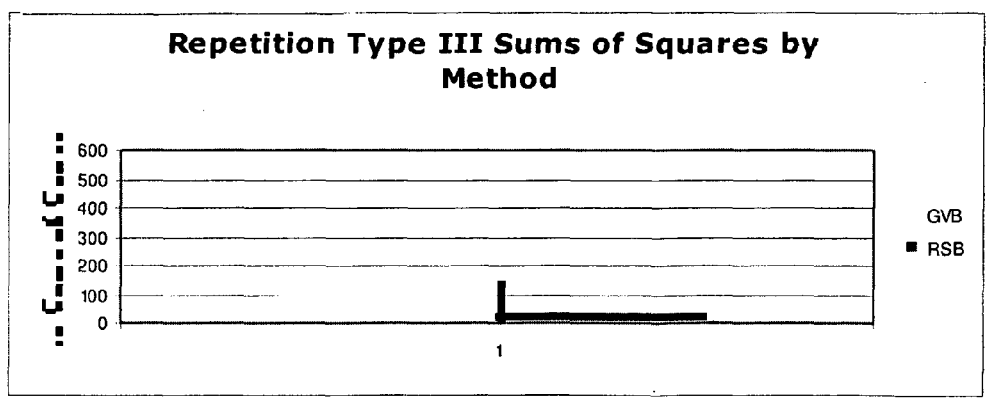

Results:

As shown in FIGS. 2A and 2B, the rumen fluid priming procedure described herein reduced run-to-run error by a factor of 10. FIG. 2A is a histogram showing a head-to-head comparison of repeated tests using the conventional Goering & Van Soest assay ("GVA" in FIG. 2A) versus the present invention ("RSA" in FIG. 2A, designating the term "rumen fluid standardization assay.") As can be seen from the statistical analysis (repetition sums of the squares), the present invention yield a statistically significant reduced variability, run-to-run ($p<0.05$). In FIG. 2A, the rumen fluid inoculum was taken from a single cow. Similar results are seen in FIG. 2B, which depicts the results of a parallel set of runs in which the rumen fluid inoculum was pooled from two cows. In FIG. 2B, "GVB" designates the Goering & Van Soest assay; RSB designates the inventive method described herein.

The reduced run-to-run variability is important because it allows values from different runs to be compared with greater confidence that the values generated in any one particular run will be comparable, on a head-to-head basis, with the values generated in any other particular run performed using the inventive method.

Figure 3B:
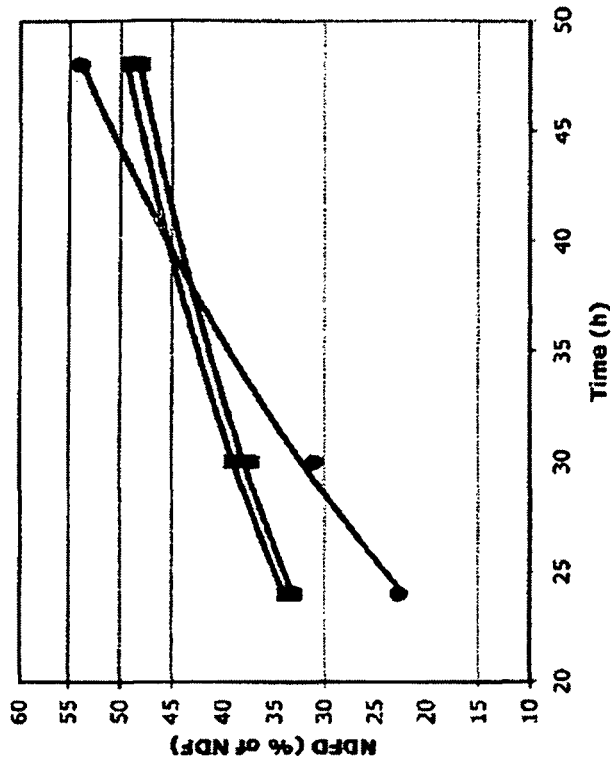
FIG. 3B a parallel graph depicting NDFD over time for triplicate runs performed by a commercial lab using the Goering & Van Soest method. The present invention yields vastly reduced run-to-run variability as compared to the conventional methodology.
Figure 3A:
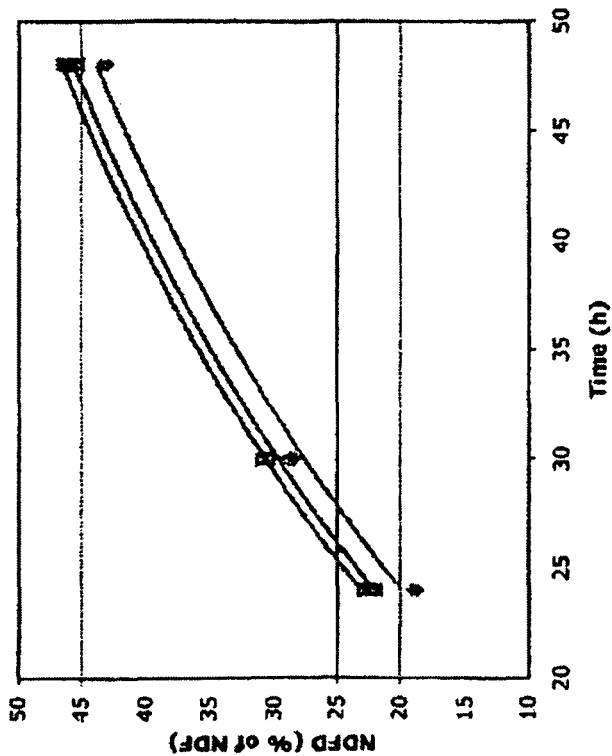
FIG. 3A is a graph depicting NDFD over time for triplicate runs as determined using the preferred version of the invention (nine (9) samples per time point analyzed in duplicate, averaged)

The present invention also yields reduced standard error as compared to results obtained from a commercial testing lab. The results are depicted in FIGS. 3A and 3B. In FIG. 3A, the present invention as described in Example 1 was run repetitively and samples taken at 24, 30, and 48 hours (nine (9) values at each time point.) The results of the three replicate experiments are shown in FIG. 3A. As can be seen from the figure, the results are closely matched. In contrast, when the same set of experiments was performed by a commercial lab (results shown in FIG. 3B), the results were far more variable. There was a repetition and time interaction ($p<0.000\ 1$) evident for the commercial laboratory which was not observed using the invention described in example 1. These results are important because they show not only does the present invention yield reduced run-to-run variability, but also that the invention performed better than the commercial methods that are commonly in use today to measure NDFD.

Example 2

In this Example, an in vitro reference technique was to calibrate the NIRS instrument using a sample set consisting of 122 ground forage samples collected from commercial nutritionists and the University of Wisconsin-Marshfield Soils & Forage Laboratory Marshfield, Wis.). Each forage sample was digested in three separate repetitions, for 24, 30, and 48 h with duplicate sub-samples for each repetition and time point combination. Eighteen forages were analyzed in each repetition, with an alfalfa silage internal standard included in each repetition.

The Research Animal and Resource Center of the College of Agriculture and Life Sciences, University of Wisconsin-Madison approved the experimental protocol. Approximately 0.5 g of each dried, ground forage sample was weighed into tared, labeled filter bags (F57, Ankom Technology, Macedon, N.Y.), which then were heat-sealed. The bags remained sealed for the entire procedure.

Two solutions, A and B, were created. Solution A contained: 18.0 L distilled $H_2O$, 102.6 g $Na_2HPO_4$, 111.6 g $KH_2PO_4$, and 10.5 g $MgSO_4.7H_2O$. Solution B contained: 13.2 g $CaCl_2.2H_2O$, 10.0 g $MnCl_2.4H_2O$, 1.0 g $CoCl_2.6H_2O$, 8.0 g $FeCl_3.6H_2O$, and was brought to 100 ml with distilled $H_2O$.

For each repetition, the day prior to inoculation at approximately 1500 h, filter bags containing sample were placed in 125 ml Erlenmeyer flasks, one bag per flask, secured in a shaking, heated (39° C.) water bath. A mineral solution was then prepared for each repetition that contained: 4000 ml distilled $H_2O$, 2000 ml Solution A, 16.0 g trypticase peptone, 0.8 ml Solution B, and 8.0 ml resazurin indicator (0.1% w/v).

A 30 ml aliquot of mineral solution was added to each 125 Erlenmeyer flask. All flasks were sealed with a two-hole rubber stopper. Each rubber stopper was fitted with two glass tubing pieces, one sealed with a rubber policeman with 4 mm vertical cut and the other attached to a gas manifold for continuous $CO_2$ gassing. The flasks containing mineral or mineral-buffer solution, and filter bags with sample were purged with $CO_2$ for 15 min and warmed overnight. Also the day prior to inoculation, reducing solution was also prepared that contained: 1.875 g Cysteine HCl, 1.875 g $Na_2S.9H_2O$, 290 ml distilled $H_2O$, and 12 ml 1N NaOH. A primer, formulated to be similar to donor cow diet, was also made and consisted of (% of DM): 40% cellulose (Whatman #42 ashless filter paper, Whatman International Ltd., Maidstone, England, ground to pass a 1 mm screen), 20% urea, 20% corn starch, and 20% cellobiose.

At approximately 6:30 h the day of inoculation, all flasks were purged continuously with $CO_2$. At 6:45 h, approximately 1 L of rumen fluid was collected from each of two cannulated, lactating cows into pre-warmed, glass-lined thermoses. The donor cows were fed a 97% forage and 3% concentrate diet ad libitum, once daily at 700 h. The rumen fluid inoculum was strained through 4 layers of cheesecloth while being gassed continuously with $CO_2$ and strained fluid from each cow was pooled in a 2000 ml Erlenmeyer flask.

Also at 6:30 h the day of inoculation, in each of six 1000 ml side-arm Erlenmeyer flasks, 0.3125 g of primer was combined with 250 ml buffer solution and 40 ml reducing solution. The 1000 ml flasks were gassed with $CO_2$ for 15 minutes while rumen fluid inoculum was collected. At 6:45 h, 250 ml strained, pooled rumen fluid was added to each 1000 ml flask in 50 ml increments in a sequential order. The flasks were then sealed with a rubber stopper, set in an incubating (39° C.) shaker and allowed to reach 37.4 mm Hg, which corresponded to 30 ml of gas produced per flask. The amount of gas production to reach 37.4 mm Hg was determined through manual calibration by forcing known amounts of gas into a sealed 1000 ml side-arm flask and reading corresponding pressures with an electronic pressure sensor. After the 1000 ml flasks averaged 37.4 mm Hg per flask, the contents of the 1000 ml Erlenmeyer flask were recombined under $CO_2$ and used to inoculate the forage samples with 22 ml inoculum solution per flask.

At approximately 1500 h the day of inoculation and each following day, all remaining filter bags were deflated with a plastic rod, while purging the in vitro flask with $CO_2$. Samples were removed at three time points, 0, 24, 30, and 48 hours after inoculation. Rinsing forage sample bags with cold, distilled water until effluent was clear terminated the fermentations. Sample NDF content was determined using a neutral detergent solution containing α-amylase and sodium sulfite using the procedure described by Goering and Van Soest (1970) adapted for an Ankom[200] Fiber Analyzer (Ankom Technology, Macedon, N.Y.). Neutral detergent fiber percentages were determined using the following equation:

NDF (% of DM)=[((bag wt+residue)−(bag wt.×bag correction factor))/((bag wt+sample)−(bag wt.)]× 100

The bag correction factor is the weight of an empty, sealed bag divided by the weight of the same bag after going through the in vitro procedure. Neutral detergent fiber digestibility was determined using the following equation:

NDFD (% of NDF)=100×[(NDF0 hour−NDFresidue)/ (NDF0 hour)]

NIRS Analysis:

Following ivNDFD analysis of all forages, ground forage samples were packed into a cylindrical sample holder equipped with a quartz window and then scanned between 400 and 2498 nm according to the procedures of Marten et al. (1983) "Quality Prediction of Small Grain Forages by Near Infrared Reflectance Spectroscopy," *Crop Sci* 23:94-96 on a near-infrared reflectance spectrophotometer (model 6500; FOSS-NIR System, Silver Spring, Md.) fit with a spinning cup holder. Forage sample data included NDF, 24, 30, and 48 h ivNDFD for universal calibration equation development.

Calibrations were computed using partial least squares regression techniques by evaluating different math transformations and different numbers of terms in the models. The optimum number of partial least squares terms was determined through maximizing the coefficient of determination while minimizing the standard error of calibration. Calibration performance was evaluated using cross validation (Shenk and Westerhaus, (1991) "Population definition, sample selection, and calibration procedures for near infrared reflectance spectroscopy," *Crop Sci.* 31:469-474) where prediction error was evaluated by dividing the calibration samples into subsets (n=4) with one subset reserved for validation and the remaining subsets used for calibration. Cross validation was completed until all subsets were used for validation once. The strength of calibration performance was based on the coefficient of determination ($R^2$), the standard error of calibration (SEC), the standard error of cross validation (SECV), and 1 minus the variance ratio (1−VR).

Results and Discussion of Example 2:

The universal sample set used for calibration consisted of six different species (Table 1); Alfalfa (*Medicago sativa*), Kura (*Trifolium ambiguum*), Timothy (*Phleum pratense*), Orchardgrass (*Dactylis glomerata*), Reed canarygrass (*Phalaris arundinacea*), and Wheat (*Triticum aestivum*). Sample maturity and storage ranged from fresh and freeze dried to mature and ensiled. The calibration set was meant to capture a broad range in NDF digestibility. Previous estimates of ivNDFD, however, were not available. The approximately 50 unit or greater ranges observed for 24, 30, and 48 h for both ivNDFD and ivdNDF suggest the sample range objective was achieved (Table 2).

TABLE 1

Summary of Sample Set Used for Universal Near-Infrared Reflectance Spectroscopy Calibration Equation Development

| | Sample Storage Type | | |
|---|---|---|---|
| | Dry | Silage | Fresh |
| Forage Type | Number of Samples | | |
| Alfalfa | 8 | 88 | |
| Kura | | 1 | 3 |
| Timothy | 4 | 5 | |
| Orchard Grass | | 5 | |
| Reed Canary Grass | | | 4 |
| Wheat | | | 1 |
| Wheat Straw | 1 | 2 | |

Previous attempts to predict NDF digestion kinetic parameters have been unsuccessful. For example, Jung et al. (1998) "Forage quality variation among maize inbreds: in vitro fiber digestion kinetics and prediction with NIRS," *Crop Sci.* 38:205-210, were unable to predict NDF degradation rates (% $h^{-1}$) or potential degradability (%) or lag time (h) with $R^2$-values greater than 0.85. Mathison et al. (1999) "Prediction of composition and ruminal degradability characteristics of barley straw by near infrared reflectance spectroscopy," *Can. J. Anim. Sci.* 79:519-523 were also unable to predict ruminal NDF degradation rate and potential degradability accurately. As a result, the present work focused on predicting NDF digestion at 24-, 30-, and 48-h time points rather than predicting kinetic parameters.

TABLE 2

Summary statistics for 122 samples analyzed using the Goeser et al. (submitted) in vitro NDF digestibility technique

| Item | NDF | ivNDFD[1] - 24 h, % of NDF | ivNDFr[2] - 24 h, % of NDF | ivNDFD - 30 h, % of NDF | ivNDFr - 30 h, % of NDF | ivNDFD - 48 h, % of NDF | ivNDFr - 48 h, % of NDF |
|---|---|---|---|---|---|---|---|
| Mean | 41.20 | 28.85 | 29.75 | 35.87 | 26.86 | 47.17 | 22.02 |
| St Dev | 10.89 | 7.42 | 10.34 | 8.35 | 9.76 | 8.76 | 7.92 |
| Max | 76.37 | 56.35 | 69.54 | 73.11 | 65.05 | 84.59 | 56.52 |
| Min | 22.17 | 7.54 | 13.26 | 10.67 | 9.72 | 24.49 | 5.57 |
| Range | 54.19 | 48.82 | 56.28 | 62.44 | 55.33 | 60.11 | 50.96 |

[1]ivNDFD = in vitro NDF digestibility, % of NDF
[2]ivNDFr = in vitro NDF residue remaining, % of DM The 48 h ivNDFD NIRS calibration statistics presented here can be compared to two prior studies. A calibration equation $R^2$-value greater than 0.85 may be considered a successful calibration (Mentink et al. (2006), supra). However, the errors of calibration and cross-validation must also be considered. Andres et al. (2005), supra, presented $R^2$, SEC, and SECV values for 48 h ivNDFD of 0.91, 2.40, and 3.90. The calibration equation statistics for 48 h ivNDFD depicted in Example 2 are improved compared with the aforementioned study (see Table 3), with $R^2$, SEC, and SECV values of 0.93, 2.31, and 3.68. The Andres et al. (2005) calibration set consisted of 62 herbage samples and were analyzed using cannulated ewes compared to the 122-sample set using cannulated dairy cows as rumen fluid donors used in this Example. Hence, the sample set used here is more robust than that used by Andres et al. (2005), likely because of the larger size and sample diversity. Mentink et al. (2006) also reported 48 h ivNDFD $R^2$, SEC, and SECV calibrations statistics for TMR samples of 0.72, 3.18, and 3.81. Again, the 48 h ivNDFD calibration statistics found in this Example 2 compared favorably. Based upon these two comparisons, it appears the improvement in precision with the present in vitro technique resulted in an improvement in NIRS calibration development. No comparisons with previous research could be made for 24 and 30 h ivNDFD calibrations. To the inventors' knowledge, this is the first report of NIRS calibrations for the 24- and 30-hour time points. As mentioned previously, an $R^2$-value of greater than 0.85 is deemed acceptable. The 24- and 30-hour ivNDFD calibration equations presented in this Example 2 were successful with $R^2$-values of 0.93 and 0.94.

TABLE 3

Universal Near-infrared reflectance spectroscopy calibration equation statistics for in vitro NDF digestibility (% of NDF) using the Goeser et. (submitted) in vitro NDF digestibility technique as a reference procedure

| Item | Math Trt | N[1] | Mean | SD[2] | Est Min | Est Max | SEC[3] | $R^2$ | SECV[4] | 1 – VR[5] |
|---|---|---|---|---|---|---|---|---|---|---|
| NDF | 2.3.3.1 | 115 | 40.32 | 9.95 | 10.47 | 70.17 | 0.88 | 0.99 | 1.28 | 0.98 |
| NDFD24 | 3.3.3.1 | 119 | 29.11 | 7.31 | 7.18 | 51.04 | 2.00 | 0.93 | 3.66 | 0.75 |
| NDFD30 | 3.2.2.1 | 116 | 35.86 | 7.11 | 15.55 | 57.18 | 1.76 | 0.94 | 4.29 | 0.64 |
| NDFD48 | 3.4.4.1 | 115 | 47.25 | 8.51 | 21.74 | 72.77 | 2.31 | 0.93 | 3.68 | 0.81 |

[1]Math Trt = in order; the derivative function, segment length (nm), segment length of first smoothing (nm), and segment length of second smoothing (nm).
[2]N = number of samples used in NIRS calibration
[3]SD = standard deviation of preditions
[4]SEC = standard error of calibration
[5]SECV = standard error of cross-validation
[6]1 – VR = 1 minus the variance ratio The in vitro digestible NDF calibration equation statistics were approaching the level of precision of the NDF calibration equation (Table 4), and as previously discussed, the NDF NIRS calibrations are accepted as precise. These observations indicate that the precision with the 24-, 30-, and 48-hour ivdNDF NIRS calibrations were significantly improved. For example, Jung et al. (1998) reported $R^2$, SEC, and SECV values for 24- and 48-hour dNDF (in vitro) of 0.84, 2.6, 3.0 and 0.90, 1.7, and 2.1, respectively. Andres et al. (2005) reported 24 and 48 h values of 0.91, 4.97, 5.83 and 0.93, 4.01, and 4.64, respectively. Our observed 24 and 48 h dNDF calibration statistics yielded markedly greater R2 (0.99 and 0.97), and lower SEC (1.07 and 1.16) and SECV (1.96 and 1.55) values than both of the previously mentioned studies (Table 4). It should be noted that Jung et al. (1998), used a modified Goering and Van Soest (1970) in vitro technique and Andres et al. (2005) utilized an in situ technique to calibrate NIRS. These observations indicate that the present invention offered greater precision than a modified Goering and Van Soest (1970) in vitro or ruminal in situ NDF digestion reference technique.

By using an improved ivNDFD assay as a reference, near-infrared reflectance spectroscopy spectral data was successfully related to in vitro NDFD and dNDF data. The universal calibration equations developed are capable of precisely predicting 24-, 30-, and 48-hour in vitro NDF digestion measurements rapidly for a broad range of forage samples.

Example 3

The objective of this Example was to determine if a rumen fluid priming technique would improve ivNDFD precision relative to a modified Goering and Van Soest (1970) technique by reducing repetition variance.

In Experiment A, a rumen fluid inoculum priming technique was compared to a modified Goering and Van Soest (1970) ivNDFD technique and both techniques used rumen fluid inoculum from a single lactating cow. In Experiment B, the rumen fluid priming technique used in Experiment A was compared to a rumen fluid priming technique and a modified Goering and Van Soest (1970) ivNDFD technique that both used inoculum collected and pooled from two lactating dairy cows.

Two experiments (A and B) were completed comparing 24-hour in vitro NDF digestibilities obtained using modified

TABLE 4

Universal Near-infrared reflectance spectroscopy calibration equation statistics for in vitro NDF residue remaining after digestion (% of DM) using the Goeser et. (submitted) in vitro NDF digestibility technique as a reference procedure

| Item | Math Trt[1] | N[2] | Mean | SD[3] | Est Min | Est Max | SEC[4] | $R^2$ | SECV[5] | 1 − VR[6] |
|---|---|---|---|---|---|---|---|---|---|---|
| NDF | 2.3.3.1 | 115 | 40.32 | 9.95 | 10.47 | 70.17 | 0.88 | 0.99 | 1.28 | 0.98 |
| NDFr24 | 3.3.3.1 | 118 | 28.97 | 9.39 | 0.78 | 57.15 | 1.07 | 0.99 | 1.96 | 0.96 |
| NDFr30 | 3.3.3.1 | 118 | 26.09 | 8.85 | 0.00 | 52.65 | 0.98 | 0.99 | 1.95 | 0.95 |
| NDFr48 | 3.4.4.1 | 113 | 21.06 | 6.87 | 0.45 | 41.67 | 1.16 | 0.97 | 1.55 | 0.95 |

[1]Math Trt = in order; the derivative function, segment length (nm), segment length of first smoothing (nm), and segment length of second smoothing (nm).
[2]N = number of samples used in NIRS calibration
[3]SD = standard deviation of preditions
[4]SEC = standard error of calibration
[5]SECV = standard error of cross-validation
[6]1 − VR = 1 minus the variance ratio The ivNDFD and ivdNDF NIRS calibration results collectively show improved NIRS calibrations relative to previous attempts. Prior calibrations for in vitro NDF digestion measurements have been poorer presumably because of poor precision with the in vitro or in situ reference techniques. However by using an improved in vitro NDF assay as a reference technique the present invention has overcome these prior limitations. Historically, precision at early in vitro time points, such as 24 h, has been so poor calibrations were not attempted. Yet the present invention achieved similar NIRS equation accuracy among all time points and the 24-, 30-, and 48-hour calibration statistics were comparable within both NDFD (% of NDF) and dNDF (% of DM) calibrations.

The equations developed are useful for predicting NDF digestibility rapidly and repeatedly by commercial laboratories over a range of time points. This invention gives ruminant nutritionists the option to predict NDF digestion for multiple realistic rumen retention times, such as 30 hours, which is between the approximate range of 27 to 32 hours observed by Oba and Allen (2000) "Effects of brown midrib 3 mutation in corn silage on productivity of dairy cows fed two concentrations of dietary neutral detergent fiber: 1. Feeding behavior and nutrient utilization," *J. Dairy Sci.* 83(6):1333-1341. The predictions at several time points can also then be used to predict digestibility for actual calculated rumen retention time.

Goering and Van Soest (1970) techniques and rumen fluid priming techniques in a randomized complete block design. An alfalfa silage sample was dried at 60° C. for 48 h, ground to pass a 1-mm Wiley mill screen (Arthur H. Thomas, Philadelphia, Pa.), and used as a forage substrate in experiments A and B. Alfalfa silage samples were analyzed by Dairyland Laboratories, Inc. (Arcadia, Wis.) by AOAC (2006) methods for DM (method 930.15), CP (method 954.01), and ash (method 942.15). Lignin and ADF were determined using methods described by Goering and Van Soest (1970).

Experiment A:

Approximately 0.5 g of dried, ground alfalfa silage sample was weighed into tared, labeled filter bags (F57, Ankom Technology, Macedon, N.Y.), which then were heat-sealed. Each repetition included 13 samples, two blank filter bags, and two zero-hour samples and five ivNDFD repetitions were completed for each of the two techniques being compared: a rumen fluid inoculum priming ivNDFD technique (RPA) and a modified Goering and Van Soest (1970) ivNDFD technique (GVA). Both techniques were completed using inoculum collected from one cannulated lactating dairy cow.

In vitro Solution and Sample Preparation:

Two solutions, A and B, were formulated. Solution A contained: 18.0 L distilled $H_2O$, 102.6 g $Na_2HPO_4$, 111.6 g $KH_2PO_4$, and 10.5 g $MgSO_4.7H_2O$. Solution B contained:

13.2 g $CaCl_2.2H_2O$, 10.0 g $MnCl_2.4H_2O$, 1.0 g $CoCl_2.6H_2O$, 8.0 g $FeCl_3.6H_2O$, and was brought to 100 ml with distilled $H_2O$.

For each repetition, the day prior to inoculation at approximately 15:00 h, filter bags containing sample were placed in 125 ml Erlenmeyer flasks, one bag per flask, secured in a shaking, heated (39° C.) water bath. A mineral solution was then prepared for each rep that contained: 800 ml distilled $H_2O$, 400 ml Solution A, 4.0 g trypticase peptone, 2.0 ml Solution B, and 2.0 ml resazurin indicator (0.1% w/v).

A 30-ml aliquot of mineral solution was added to each flask designated to the RPA. Six hundred ml of remaining mineral solution was then combined with 200 ml of a buffer solution that contained: 18.0 L distilled $H_2O$, 630 g $NaHCO_3$, and 72.0 g $NH_3\_HCO_3$.

A 40-ml aliquot of mineral-buffer solution was added to each flask designated to the GVA. All flasks were sealed with a two-hole rubber stopper. Each rubber stopper was fitted with two glass tubing pieces, one sealed with a rubber policeman with a 4 mm vertical cut and the other attached to a gas manifold for continuous $CO_2$ gassing. The flasks containing mineral or mineral-buffer solution, and filter bags with sample were purged with $CO_2$ for 15 min and warmed overnight. The day prior to inoculation, reducing solution was also prepared that contained: 0.505 g Cysteine HCl, 0.505 g $Na_2S.9H_2O$, 76.8 ml distilled $H_2O$, and 3.2 ml 1N NaOH.

Rumen Fluid Collection and GVA Flask Inoculation:

The experimental protocol was approved by the Research Animal and Resource Center of the College of Agriculture and Life Sciences, University of Wisconsin-Madison. At approximately 06:30 h the day of inoculation, all flasks were purged continuously with $CO_2$ and 2 ml of reducing solution was added to each flask designated to the GVA. At 06:45 h, approximately 1 L of rumen fluid was collected from one cannulated, lactating cow into a pre-warmed, glass-lined thermos. The donor cow was fed a 60% forage, alfalfa and corn silage, and 40% concentrate diet ad libitum, once daily at 07:00 h. The rumen fluid inoculum was transported to the laboratory and in a warm (39° C.) room, strained through four layers of cheesecloth while being gassed continuously with $CO_2$. Approximately 800 ml of strained rumen fluid was used to immediately inoculate the GVA flasks with 10 ml rumen fluid inoculum per flask. The period of time from rumen fluid collection to GVA flask inoculation was approximately 15 minutes.

Rumen Fluid Priming Technique and RPA Flask Inoculation:

At 06:30 h the day of inoculation, 2.5 g of crystalline cellulose ground to pass a 1-mm Wiley screen (Whatman 42 Ashless Filter Paper Circles, Whatman Int. Ltd., England) was combined with 200 ml buffer solution and 40 ml reducing solution in a 1000 ml side-arm Erlenmeyer flask. The 1000 ml Erlenmeyer flask was gassed with $CO_2$ for 15 minutes while rumen fluid inoculum was collected. At 06:45 h, 200 ml of filtered rumen fluid was added to the 1000 ml side-arm Erlenmeyer flask containing ground cellulose, reducing and buffer solution. The flask was then sealed with a rubber stopper, set in an incubating (39° C.) shaker and allowed to reach 46.7 mm Hg, which corresponded to 60 ml of gas produced or 0.3 ml gas production per ml rumen fluid inoculum. The amount of gas required to reach 46.7 mm Hg was determined via manual calibration by forcing known amounts of gas into a sealed 1000 ml side-arm flask and reading corresponding pressures with the pressure meter. After reaching 46.7 mm Hg, the contents of the flask were used to inoculate the RPA samples (22 ml per flask).

Sample Analysis:

At approximately 15:00 h for each repetition, filter bags for both methods were deflated by tamping each filter bag down with a plastic rod while purging the flask with $CO_2$. Samples were removed at 0 and 24 h after inoculation for each technique. The forage fiber bags were rinsed with ambient temperature (approximately 20° C.) distilled water until effluent was clear to terminate the fermentations similar to the method described by Eun, et al. (2007).

Sample NDF content was determined using a neutral detergent solution containing α-amylase and sodium sulfite using the procedure described by Goering and Van Soest (1970) adapted for an Ankom[200] Fiber Analyzer (Ankom Technology, Macedon, N.Y.). Neutral detergent fiber percentages were determined using the following equation:

$$NDF (\% \text{ of DM}) = [((\text{bag wt.} + \text{residue}) - (\text{bag wt.} \times \text{bag correction factor}))/((\text{bag wt.} + \text{sample}) - (\text{bag wt.}))] \times 100$$

The bag correction factor is the weight of an empty, sealed bag divided by the weight of the same bag after going through the in vitro procedure. Neutral detergent fiber digestibility was determined using the following equation:

$$ivNDFD (\% \text{ of NDF}) = 100 \times [(NDF_{0\,hour} - NDF_{residue})/(NDF_{0\,hour})]$$

Statistical Analysis:

The complete data set was analyzed as a randomized complete block design with sub-sampling using SAS Proc Mixed-brand software (SAS, Cary, N.C.). The model used was:

$$Y_{ijkl} = \mu + R_i + M_j + RM_{ij} + e_{ijkl}$$

where; $Y_{ijkl}$=NDFD, dependent variable, $\mu$=population mean, $R_i$=fixed effect of repetition i, $M_j$=fixed effect of method, $RM_{ij}$=interaction between repetition and method, $e_{ijkl}$=random residual error, assumed to be normally distributed. The data sets were also separated by technique and analyzed using SAS Proc GLM-brand software (SAS, Cary, N.C.) to obtain sums of squares. The model used was:

$$Y_{ikjl} = \mu R_i + e_{ijkl}$$

where; $Y_{ijkl}$=NDFD, dependent variable, $\mu$=population mean, $R_i$=fixed effect of repetition i, $e_{ijkl}$=random residual error, assumed to be normally distributed. Repetition variance for each technique was compared using an F-test. Significance was declared at $P<0.05$. Variance within runs was evaluated using Levene's Test where analysis of variance was performed on the absolute deviance of each observation from the median of its group. See Levene (1960) in "Contributions to Probability and Statistics: Essays in Honor of Harold Hotelling," I. Olkin, S. G. Ghurye, W. Hoeffding, W. G. Madow, and H. B. Mann, eds. Stanford University Press, Stanford, Calif., pp. 278-292.

Experiment B:

The alfalfa silage sample described in Experiment A was weighed (0.5 g) into Ankom F57 filter bags as described previously. The bags were sealed and five ivNDFD repetitions were completed with 36 samples analyzed per repetition. Each repetition included eight samples, two blank filter bags, and two zer-hour samples for each ivNDFD technique. The three ivNDFD techniques used in experiment B were; the RPA described in Experiment A, a rumen fluid priming ivNDFD technique using rumen fluid inoculum pooled from two cows (RPB), and a modified Goering and Van Soest (1970) ivNDFD technique using rumen fluid inoculum pooled from two cows (GVB). Experiment B used the same cow described in Experiment A and an additional cannulated lactating Holstein cow.

In Vitro Solution and Sample Preparation:

The A buffer, B buffer, mineral, and reducing solutions were formulated as described in Experiment A. For each repetition, at approximately 15:00 h the day prior to inoculation, filter bags containing sample were placed in 125 ml Erlenmeyer flasks secured in a shaking water bath, set at 39° C. A 30 ml aliquot of mineral solution was added to each flask designated to the RSA and RSB. A 400-ml aliquot of mineral solution was combined with 133.3 ml of buffer solution and 40 ml of the mineral-buffer solution was added to each flask designated to the GVB. All flasks were then sealed with a two-hole rubber stopper. Each rubber stopper was fitted with two glass tubing pieces, one sealed with a rubber policeman with 4 mm vertical cut and the other attached to a gas manifold for continuous $CO_2$ gassing. The flasks, containing mineral or mineral-buffer solution and filter bags with sample were purged with $CO_2$ for 15 min and warmed overnight.

Rumen Fluid Collection and GVB Flask Inoculation:

The experimental protocol was approved by the Research Animal and Resource Center of the College of Agriculture and Life Sciences, University of Wisconsin-Madison. At approximately 06:30 h the day of inoculation, all flasks were purged continuously with $CO_2$ and 2 ml of reducing solution was added to each flask designated to the GVB. At 06:45 h, approximately 1 L of rumen fluid was collected from each of two cannulated, lactating cows into pre-warmed, glass-lined thermoses. The donor cows were fed a 60% forage and 40% concentrate diet ad libitum, once daily at 07:00 h. The rumen fluid inoculum was strained through 4 layers of cheesecloth while being gassed continuously with $CO_2$ and 700 ml of strained fluid from each cow was pooled in a 2 liter Erlenmeyer flask. Approximately 800 ml of strained, pooled rumen fluid was used to immediately inoculate the GVB flasks with 10 ml rumen fluid inoculum per flask. The period of time from rumen fluid collection to GVB flask inoculation was approximately 15 minutes.

Rumen Fluid Priming Techniques and RPA and RPB Flask Inoculation:

At 06:30 h the day of inoculation, in each of two 1000 ml side-arm Erlenmeyer flasks, 2.5 g of ground crystalline cellulose was combined with 200 ml buffer solution and 40 ml reducing solution. Both 1000 ml Erlenmeyer flasks were gassed with $CO_2$ for 15 minutes while rumen fluid inoculum was collected. At 06:45 h, 200 ml of strained rumen fluid from a single cow was added to one of the 1000 ml side-arm Erlenmeyer for the RPA, and 200 ml of strained, pooled rumen fluid was added to the second flask for the RPB. The flasks were then sealed with a rubber stopper, set in an incubating (39° C.) shaker and allowed to reach 46.7 mm Hg, which corresponded to 60 ml of gas production. After each flask, RPA or RPB, reached 46.7 mm Hg, the contents of the 1000 ml Erlenmeyer flask were used to inoculate the RSA or RSB samples, respectively (22 ml per flask).

Sample Analysis:

All samples were analyzed as described in Experiment A.

Statistical Analysis:

The complete data set was analyzed as a randomized complete block design with subsampling using SAS Proc Mixed (SAS, Cary, N.C.). The model used was as follows:

$$Y_{ijkl}=\mu+R_i+M_j+RM_{ij}+e_{ijkl}$$

where; $Y_{ijkl}$=NDFD, dependent variable, $\mu$=population mean, $R_i$=fixed effect of repetition i, $M_j$=fixed effect of method, $RM_{ij}$=interaction between rep and method, $e_{ijkl}$=random residual error, assumed to be normally distributed. The data sets were also separated by technique and analyzed using SAS Proc GLM (SAS, Cary, N.C.) to obtain sums of squares. The model used was as follows:

$$Y_{ijkl}=\mu+R_i+e_{ijkl}$$

where; $Y_{ijkl}$=NDFD, dependent variable, $\mu$=population mean, $R_i$=fixed effect of repetition i, $e_{ijkl}$=random residual error, assumed to be normally distributed. Repetition variance for each technique was compared using an F-test. Significance was declared at P<0.05. Variance within runs was evaluated using Levene's Test (Levene, 1960, supra) where analysis of variance was performed on the absolute deviance of each observation from the median of its group.

The in vitro methods described in Experiments A and B use Goering and Van Soest (1970) buffer, macro- and micro-mineral solutions. The in vitro techniques described here differ from that of Goering and Van Soest (1970) through the following modifications: 24-h incubation time period, the use of Ankom F57 forage fiber bags in 125 ml Erlenmeyer flasks for digestion and NDF assays, no blending of inoculum was done based upon the observations of Rymer et al. (1999), and an ambient-temperature, distilled-water rinse was used to terminate fermentations. In addition, for the priming method, the inoculum was combined with buffer and reducing solution prior to inoculation and cellulose was added to inoculum solution.

A 24-h incubation time period may be a harsher test of differences in in vitro NDFD methodology because at early stages of digestion the corresponding residue disappearances are small, thus making digestion more difficult to study. See Pell and Schofield, (1993) "Computerized monitoring of gas production to measure forage digestion in vitro," *J. Dairy Sci.* 76:1063-1073.) The use of Ankom F57 forage fiber bags may limit forage sample surface area available to rumen microbes. Fluid and sample contact was maximized by deflating forage fiber bags manually. Adesogan (2005) "Effect of bag type on the apparent digestibility of feeds in ANKOM Daisy(II) incubators," *Anim. Feed Sci. Technol.* 119: 333-344 used Ankom forage fiber bags in a bulk in vitro digestion system and observed Ankom bags gave more precise prediction ($R^2$=0.77) of the Tilley and Terry method than alternative types of forage digestion bags. Eun et al. (2007) "Use of exogenous fibrolytic enzymes to enhance in vitro fermentation of alfalfa hay and corn silage," *J. Dairy Sci.* 90:1440-1451 also used individual bags within 125 ml Erlenmeyer flasks for in vitro digestions and used cold distilled water to terminate the digestions. Using forage fiber bags reduces the losses of residue when transferring between the in vitro vessel and the NDF beaker. Without the use of forage fiber bags for sample handling, fiber particles may be retained on the sidewall of the digestion vessel during the digestion procedure and when transferring fluids to a beaker for residue NDF analysis. The use of forage fiber bags also improves the efficiency of NDF analysis of degraded residue. One person can analyze 24 in vitro samples for NDF content at one time using the Goering and Van Soest (1970) NDF procedure modified for the Ankom[200] forage fiber analyzer in approximately a two hour period using one Ankom[200] forage fiber analyzer. Efficiency can be improved beyond this level by employing multiple forage fiber analyzers, with the potential to analyze 48 or 72 samples in a similar time period. Forage fiber analyzers can offer substantial timesaving relative to the traditional Goering and Van Soest (1970) refluxing procedure.

The remaining differences between the present Example and Goering and Van Soest's (1970) in vitro rumen digestion, specifically combining rumen fluid inoculum with 12.5 mg cellulose per ml rumen fluid inoculum, buffer, and reducing solution prior to inoculation and allowing the mixture to produce 0.3 ml gas per ml rumen fluid, are unique and first reported here. The Tilley and Terry technique (1963) "A two-stage technique for the in vitro digestion of forage crops," *J. Br. Grassl. Soc.* 18:104-111, modified by Goering and Van Soest (1970) and others over the following 30 years is based upon collecting rumen fluid inoculum from one or several ruminants and promptly inoculating samples to be digested. The affects of time from rumen fluid inoculum collection to sample inoculation prior to in vitro gas production studies has been summarized in a review by Mould et al. (2005) "In vitro microbial inoculum: A review of its function and properties," *Anim. Feed Sci. Technol.* 123:31-50. They concluded that there was no significant correlation between the time interval between collection and inoculation, and in vitro gas production. However there was not an attempt to stimulate microbial activity prior to inoculation by adding fermentable carbohydrate in any of the studies summarized in this review.

Figure 4:
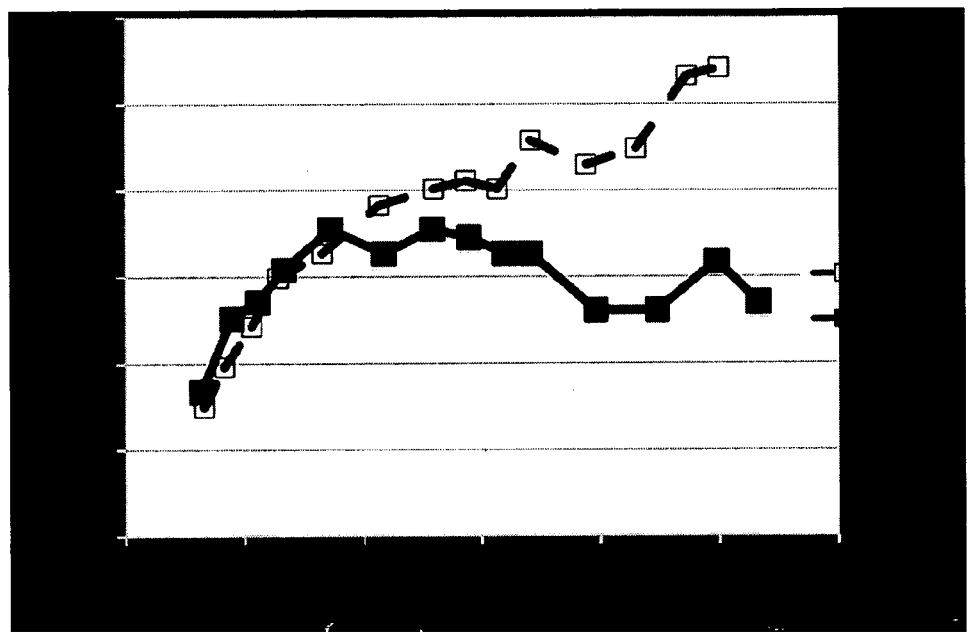
FIG. 4 is a graph depicting inter-assay variation, indicated by gas production per ml of rumen fluid inoculum, in rumen fluid inoculum gas pressure readings for a primed (12.5 mg cellulose per ml rumen fluid inoculum) and unprimed inoculum. See Example 3.

This Example is the first attempt to standardize microbial activity of rumen fluid by mixing inoculum with a substrate and allowing the inoculum to produce a predetermined amount of gas prior to sample inoculation. Cumulative gas pressure of the inoculum was used as an indicator of microbial activity. While not being limited to any underlying biological mechanism, the hypothesis was that inoculum microbial activity might be more consistent if the stresses associated with collection, (oxygen exposure, temperature changes) or the inconsistencies in activity due to normal eating and drinking behavior were accounted for by monitoring gas production and using gas pressure within the collection flask as a crude measure of microbial activity, compared to inoculum that was collected and used as quickly as feasible. A pilot study was completed prior to Experiments A and B comparing rumen fluid activity, as indicated by gas production per ml of rumen fluid, of a primed inoculum (12.5 mg cellulose per ml of rumen fluid inoculum) and an unprimed inoculum following five repetitions. Gas production over time varied, but inter-assay variance of gas produced per ml of rumen fluid became more consistent after rumen fluid inoculum produced approximately 0.1 ml gas per ml rumen fluid with the primed inoculum. See FIG. 4. Inter-assay variance continued to increase in the unprimed inoculum as the inoculum continued to produce gas. Results of the pilot study suggested that rumen fluid activity was reaching a consistent activity after priming the inoculum and allowing greater than 0.1 ml gas production per ml rumen fluid.

Nutrient composition for the alfalfa silage used in both Experiments A and B is presented in Table 5. In Experiment A, both techniques used inoculum from a single donor cow. The amount of time for the flasks to reach 46.7 mm Hg ranged from 2 to 5.5 hours. The rumen fluid priming technique decreased (P<0.024) repetition sums of squares for 24 h ivNDFD compared to a modified Goering and Van Soest (1970) technique (see Table 6). This observation suggests primed rumen fluid, from a single donor animal, reduced some of the variable nature of rumen fluid inoculum. Priming provided a measure of standardization beyond collecting rumen fluid inoculum from the same animal, on a prescribed diet, at the same time each day (prior to feeding). Both methods displayed comparable intra-assay error. Levene's test was insignificant for each repetition and method (Table 6). The standard deviations of means for each method and repetition also did not exhibit any patterns.

TABLE 5

Experiment A and B alfalfa silage nutrient composition

| Item | % of Dry Matter |
|---|---|
| NDF | 43.83 |
| ADF | 39.73 |
| CP | 21.12 |
| Lignin | 8.71 |
| Fat | 2.42 |
| Ash | 9.41 |

TABLE 6

In vitro NDF digestion parameters for two in vitro techniques in experiment A

| | ivNDFD[1] Technique | | | |
|---|---|---|---|---|
| Item | GVA | RSA | SEM[2] | F-value[3] | P< |
| Repetition sum of squares[4] | | | | |
| | 503.31 | 51.17 | | 9.836 | 0.024 |
| Repetition ivNDFD, % of NDF[5] | | | | |
| 1 | 24.70 ± 3.40 | 21.84 ± 3.29 | | | |
| 2 | 26.71 ± 3.34 | 23.41 ± 3.93 | | | |
| 3 | 21.74 ± 3.55 | 21.34 ± 4.87 | | | |
| 4 | 28.92 ± 3.75 | 23.65 ± 4.02 | | | |
| 5 | 21.84 ± 4.14 | 22.34 ± 5.03 | | | |
| Repetition mean absolute deviation from median of each group, % of NDF (Levene's Test)[6] | | | | |
| 1 | 2.803 | 2.703 | | | |
| 2 | 2.754 | 2.720 | | | |
| 3 | 3.061 | 4.343 | | 0.47 | NS |
| 4 | 2.898 | 3.045 | | | |
| 5 | 3.002 | 3.684 | | | |
| Mean 24 h ivNDFD, % of NDF[7] | 24.78$^a$ | 22.52$^b$ | 0.4868 | | 0.0014 |

[1]ivNDFD Techniques = GVA: modified Goering and Van Soest (1970), RSA: rumen fluid inoculum standardization; both techniques used inoculum from a single cow.
[2]SEM = Standard error of the treatment mean.
[3]F-value = larger sum of squares value/smaller sum of squares value on 4, 4 degrees of freedom.
[4]Repetition Type III sum of squares = sum of squares attributed to repetition following ANOVA.
[5]Repetition ivNDFD, % of NDF = mean ivNDFD as a % of NDF for each technique and repetition, each value is the mean of 13 observations ± standard deviation.
[6]Repetition mean absolute deviation from median of each group, % of NDF = Variable for Levene's Test, analysis of variance completed on absolute deviation from median of each group for each observation.
[7]Mean 24 h ivNDFD, % of NDF = means with differing superscript differ (P < 0.05)

Figure 5:
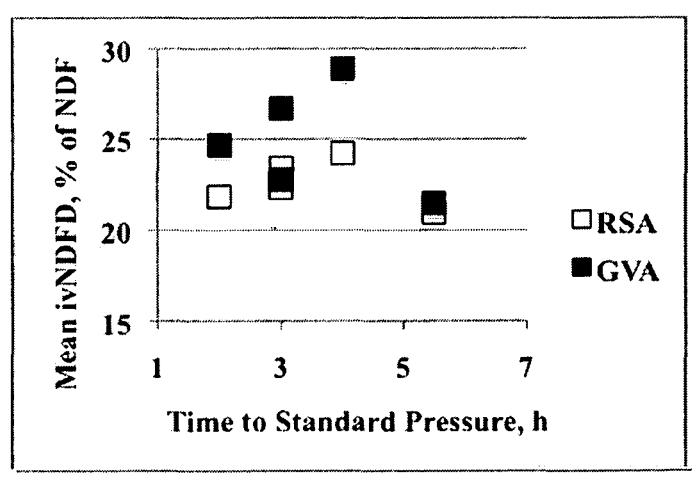
FIG. 5 is a graph depicting the relationship between repetition mean in vitro NDF digestibility (ivNDFD) and the time required for inoculum to reach standard pressure (priming technique) in Experiment A of Example 3. The unprimed inoculum was plotted against the time to pressure of the corresponding priming technique. No significance was observed.
Figure 6:
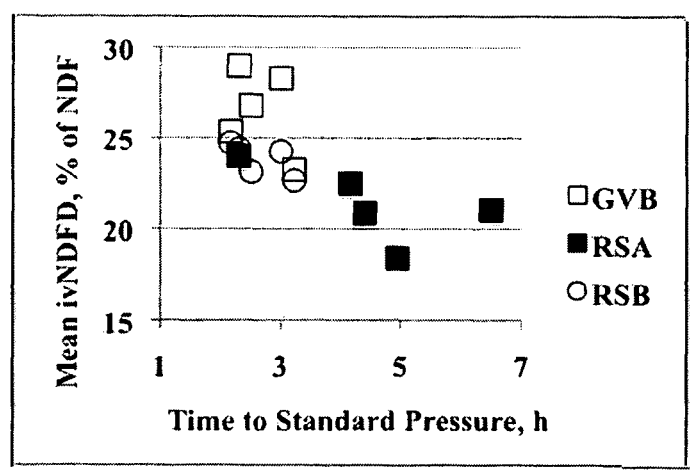
FIG. 6 is a graph depicting the relationship between repetition mean in vitro NDF digestibility (ivNDFD) and the time required for inoculum to reach standard pressure (priming technique) in Experiment B of Example 3. The unprimed inoculum was plotted against the time to pressure of the corresponding priming technique. No significance was observed.

While priming improved repeatability, the RPA also significantly decreased 24-h ivNDFD relative to the GVA. The decreased ivNDFD most likely resulted from an increase in substrate-to-inoculum ratio by priming inoculum with cellulose. The RPA flasks contained 12.5 mg more substrate per flask than did the GVA flasks. The sample-to-inoculum ratios were 50 and 62.5 mg substrate per ml of rumen fluid inoculum for GVA and RPA, respectively, and were within the range of substrate-per-ml rumen fluid calculated from reviews by Getachew et al. (1998) "In vitro gas measuring techniques for assessment of nutritional quality of feeds: a review," *Anim. Feed Sci. Technol.* 72: 261-281, and Rymer et al. (2005) "In vitro cumulative gas production techniques: History, methodological considerations and challenges," *Anim. Feed Sci. Technol.* 123:9-30. However, the unprimed vessels contained 25% less substrate. The period of time to reach 46.7 mm Hg was not an index of inoculum activity. The time to reach 46.7 mm Hg for each repetition was not related to average NDFD from that repetition for both Experiments A and B (see FIGS. 5 and 6).

In Experiment B, the priming technique precision and the effect of pooled rumen fluid inoculum were tested. This has been suggested to reduce repetition variance, see Williams (2000) "Cumulative gas production techniques for forage evaluation," in Forage Evaluation in Ruminant Nutrition, D. I. Givens, E. Owen, R. F. E. Axford, and H. M. Omed, eds. CABI Publishing, Wallingford, UK, pp. 189-213. As observed in Experiment A, the methods appeared to exhibit decreased ivNDFD inter-assay error relative to unprimed rumen fluid inoculum, using both single cow inoculum and inoculum pooled from two donor cows. The methods did not differ in intra-assay precision, but ivNDFD precision was improved from repetition to repetition using priming techniques. The priming methods also produced significantly lower ivNDFD estimates, which most likely occurred due to an increase in substrate-to-inoculum ratio.

TABLE 7

In vitro NDF digestion parameters for three techniques in experiment B

| | ivNDFD[1] Technique | | | | | |
|---|---|---|---|---|---|---|
| Item | GVB | RSA | RSB | SEM[2] | F-value[3] | P< |
| Repetition Type III sum of squares[4] | | | | | | |
| | 163.70 | | 23.34 | | 7.01 | 0.043 |
| | | 133.12 | 23.34 | | 5.70 | 0.060 |
| Repetition ivNDFD, % of NDF[5] | | | | | | |
| 1 | 28.31 ± 3.81 | 20.84 ± 1.43 | 24.26 ± 2.73 | | | |
| 2 | 26.87 ± 1.99 | 18.40 ± 2.80 | 23.14 ± 4.33 | | | |
| 3 | 23.12 ± 3.62 | 22.51 ± 3.28 | 22.67 ± 2.48 | | | |
| 4 | 25.36 ± 2.08 | 24.08 ± 2.72 | 24.73 ± 2.87 | | | |
| 5 | 28.99 ± 3.21 | 21.06 ± 1.69 | 24.20 ± 2.65 | | | |
| Repetition mean absolute deviation from median of each group, % of NDF[6] | | | | | | |
| 1 | 2.80 | 1.17 | 1.85 | | | |
| 2 | 1.10 | 1.89 | 3.23 | | | |
| 3 | 2.32 | 2.12 | 1.83 | | | NS |
| 4 | 1.73 | 2.15 | 2.36 | | | |
| 5 | 2.14 | 1.26 | 1.61 | | | |
| Mean 24 h ivNDFD, % of NDF[7] | 26.55$^a$ | 21.43$^c$ | 23.83$^b$ | 0.47 | | 0.001 |

[1]ivNDFD Techniques = GVB: modified Goering and Van Soest (1970) using inoculum pooled from two dairy cows, RSA: rumen fluid inoculum standardization using inoculum from a single cow, RSB: rumen fluid inoculum standardization using inoculum from two cows.
[2]SEM = Standard error of the mean.
[3]F-value = largest sum of square value/smallest sum of squares value on 4, 4 degrees of freedom.
[4]Repetition Type III sum of squares = sum of squares attributed to repetition following ANOVA.
[5]Repetition ivNDFD, % of NDF = mean ivNDFD as a % of NDF for each technique and repetition, each value is the mean of 8 observations (or 7 in the case of a missing value) ± standard deviation.
[6]Repetition mean absolute deviation from median of each group, % of NDF = Variable for Levene's Test, analysis of variance completed on absolute deviation from median of each group for each observation.
[7]Mean 24 h ivNDFD, % of NDF = means with differing superscript differ (P < 0.05).

equivalent intra-assay error. The standard deviation of the means for each repetition and method did not exhibit any clear trends and Levene's test was again insignificant (Table 7). The amount of time for each flask to reach 46.7 mm Hg varied from 2 to 6.5 hours and the RPA consistently took longer to reach 46.7 mm Hg in each repetition. These observations were in accordance with Williams (2000) suggestions in that the modified Goering and Van Soest (1970) technique using pooled rumen fluid inoculum produced comparable repetition variance as the RPA (Table 7). This observation strongly suggests that priming rumen fluid inoculum from one donor animal yields similar assay precision to using pooled rumen fluid inoculum from two donor cows, and both techniques offer improved precision over using unprimed inoculum from one animal. Yet, the rumen fluid priming technique using pooled rumen fluid further reduced inter-assay error compared to the GVB and tended lower than RPA, indicating a further improvement in precision was achieved by priming pooled rumen fluid inoculum in this experiment. The ivNDFD estimates from the primed techniques were significantly lower than the modified Goering and Van Soest (1970) method (Table 7). However, primed rumen fluid inoculum pooled from two donor cows had lower inter-assay error than any other technique tested.

The collective results of both Experiments A and B indicate that the rumen fluid priming techniques described here While not being limited to any specific mechanism or biological phenomenon, it is hypothesized that providing rumen inoculum microflora a cellulose substrate and allowing the inoculum to produce 0.3 ml gas per ml rumen fluid permitted the ruminal microbial populations to propagate to a more consistent activity level, designated by a gas pressure reading, allowing repeatable 24-h ivNDFD measurements to be made. While rumen fluid inoculum is not and may never be a reagent, the primed inoculum appears to be a more consistent inoculum than unprimed fluid.

The in vitro NDF digestion technique using cellulose primed rumen fluid reduced ivNDFD inter-assay error compared with a traditional laboratory technique using inoculum from a single or two donor animals but yielded lower estimates of 24 h ivNDFD.

Example 4

This Example is provided to demonstrate that pretreating rumen fluid with a mixture of carbohydrates and urea and standardizing fermentative activity of the fluid prior to inoculating forage samples improved precision in vitro NDF digestibility estimates relative to in vitro assays where rumen fluid was not primed. This Example also demonstrates that the modified in vitro NDF digestibility assay was validated with near infrared spectroscopy, and 24-, 30- and 48-hour in vitro NDF digestibility can be predicted accurately and precisely using NIRS standard curves fabricated from digestion samples prepared as described herein.

In order to be certified by the National Forage Testing Association (NFTA), commercial forage testing laboratories must meet standards for inter- and intra-assay errors for dry matter, crude protein and neutral detergent fiber assays. However no such standard exists for in vitro neutral detergent fiber digestibility. As noted earlier, fiber digestibility is an important component of forage quality. Forage fiber digestibility can range from 20 to nearly 80 percent of the total fiber and can account for as much as 75 percent of the digestible energy of forage DM. Conventional methods for measuring fiber digestibility are not standardized, and tend to be imprecise relative to assays for DM, CP and NDF. See, for example, Mentink et al. (2006), supra. Estimates of NDF digestibility vary from lab to lab because of differences in the lab assay, which makes it difficult to compare results between labs or to incorporate fiber digestibility into ration balancing software. In addition, in vitro estimates of fiber digestibility tend to vary from run to run within a lab due to the variable activity of rumen fluid.

In commercial labs, most forage analyses are done by near infrared reflectance spectroscopy (NIRS). The precision of NIRS calibration equations are hindered, however, by the precision of the analytical technique used to calibrate the NIRS instrument (Shenk &Westerhaus, (1994), supra) and previous attempts to calibrate NIRS to ivNDFD for diverse feeds were unsuccessful because of imprecision in the laboratory technique (Andres, et al. (2005), Mentink, et al. (2006), supra). An ivNDFD analytical assay with lower intra-assay error will allow for NIRS calibrations with improved calibration statistics.

The objective of this Example was to compare in vitro NDF digestion estimates, and intra- and inter-assay error for the three in vitro NDF digestion methods. The modified priming technique was then used to calibrate NIRS using 24-, 30-, and 48-h ivNDFD data for validation of the modified priming technique precision.

Two experiments were completed. Experiment A compared three in vitro NDF digestion techniques. Experiment B evaluated NIRS calibration statistics when 24-, 30-, and 48-h ivNDFD were predicted using the modified priming technique as a reference procedure.

Experiment A—Comparing ivNDFD Estimates, Intra-, and Inter-Assay Precision of Three ivNDFD Methods:

Each of the three ivNDFD techniques evaluated in this experiment used rumen fluid inoculum collected and pooled from two ruminally cannulated, lactating dairy cows. The first method evaluated was a modified Goering and Van Soest (1970) ivNDFD technique (GV). The second method (CG) was a modification of the priming technique described by Goeser and Combs, and the third method used unprimed inoculum that had been held until it reached the same gas pressure as the CG method (UN).

Two forages, alfalfa silage and wheat straw, were analyzed with each of the three ivNDFD methods. Both forages were analyzed by Dairyland Laboratories, Inc. (Arcadia, Wis.) by AOAC (2006) methods for DM (method 930.15), CP (method 954.01), and ash (method 942.15). Lignin and ADF were determined using methods described by Goering and Van Soest (1970). See Table 8 for details.

TABLE 8

Forage sample composition in Experiment A

| | Forage | |
|---|---|---|
| Item | Alfalfa silage | Wheat straw |
| | % of Dry Matter | |
| NDF | 44.94 | 73.58 |
| ADF | 41.11 | 57.03 |
| Crude Protein | 20.62 | 6.36 |
| Lignin | 8.37 | 9.71 |
| Fat | 3.75 | 0.82 |
| Ash | 10.22 | 7.11 |

Both forages were dried at 60° C. for 48 h in a forced air oven and ground to pass a 1-mm Wiley mill screen (Arthur H. Thomas, Philadelphia, Pa.) prior to submission for chemical analysis or for in vitro fiber digestibility. The in vitro NDF digestion assays were conducted as follows:

Approximately 0.5 g of dried, ground forage sample was weighed into tared, labeled filter bags (F57, Ankom Technology, Macedon, N.Y.). The CG and UN samples were prepared and digested in a similar manner as the rumen fluid priming method and the GV samples were prepared and digested in a similar manner as the modified Goering and Van Soest technique described earlier. The forage fiber bags remained sealed for the entire procedure for each of the three methods. Five repetitions were completed and each repetition included a zero-hour, five digestion time points, and blank samples analyzed in triplicate for each of the three techniques described.

While the forage samples were prepared in a similar manner, the CG and UN methods used different rumen fluid inoculum preparation procedures.

Rumen Fluid Collection and GV Flask Inoculation:

The Research Animal and Resource Center of the College of Agriculture and Life Sciences, University of Wisconsin-Madison approved the experimental protocol. At approximately 06:30 h the day of inoculation, all flasks were subjected to continuous $CO_2$ flow and 2 ml of reducing solution was added to each flask designated to the GV. At 06:45 h, approximately 1 L of rumen fluid was collected from each of two cannulated, lactating cows into pre-warmed, glass-lined thermoses. The donor cows were fed a 97% forage and 3% concentrate diet ad libitum, once daily at 07:00 h. The rumen fluid inoculum was strained through four layers of cheesecloth while under $CO_2$ flow and fluid from each cow was pooled in a 2000 ml Erlenmeyer flask. Approximately 800 ml of strained, pooled rumen fluid was used to immediately inoculate the GV flasks with 10 ml rumen fluid inoculum per flask. The period of time from rumen fluid collection to GV flask inoculation was approximately 15 minutes.

CG Primer:

The CG primer, formulated to be similar to the donor cows diet, was made and consisted of (% of DM): 40% cellulose (Whatman #42 ashless filter paper, Whatman International Ltd., Maidstone, England), ground to pass a 1 mm screen, 20% urea, 20% corn starch, and 20% cellobiose.

CG Rumen Fluid Priming Procedure and CG and UN Flask Inoculation:

At 06:30 h the day of inoculation, 0.3125 g of primer was combined with 250 ml buffer solution and 40 ml reducing solution in each of two 1000 ml side-arm Erlenmeyer flasks designated for the CG method. Two separate 1000 ml sidearm Erlenmeyer flasks containing only 250 ml buffer and 40 ml reducing solution were used for the UN method. The UN method was not primed with CG primer. All 1000 ml flasks were gassed with $CO_2$ for 15 minutes while rumen fluid inoculum was collected. At 06:45 h, 250 ml strained, pooled rumen fluid was added to each of the CG and UN 1000 ml flasks. The CG and UN flasks were then sealed with a rubber stopper, set in an incubating (39° C.) shaker and allowed to reach 37.4 mm Hg pressure, which corresponded to 30 ml of gas production or 0.12 ml gas production per ml rumen fluid inoculum. The amount of gas production to reach 37.4 mm Hg was determined through manual calibration by forcing known amounts of gas into a sealed 1000 ml side-arm flask and measuring corresponding pressures with an electronic pressure sensor. After CG or UN flasks averaged 37.4 mm Hg per flask, the contents of the 1000 ml Erlenmeyer flasks were recombined under $CO_2$ and used to inoculate the UN or CG samples with 22 ml inoculum solution per flask.

Sample Analysis:

At approximately 15:00 h each day, all remaining forage fiber bags were deflated with a plastic rod while purging the in vitro flask with $CO_2$. Samples were removed at five time points after inoculation; 24, 28, 48, 54, and 72 hours. The fermentations were terminated by rinsing the bags with ambient-temperature distilled water until the effluent was clear, similar to the technique described by Eun, et al. (2007), supra. Sample NDF content was determined using a neutral detergent solution containing α-amylase and sodium sulfite using the procedure described by Goering and Van Soest (1970) adapted for an Ankom[200] Fiber Analyzer (Ankom Technology, Macedon, N.Y.). Neutral detergent fiber percentages were determined using the following equation:

NDF (% of DM)=[((bag wt.+residue)−(bag wt.×bag correction factor))/((bag wt.+sample)−(bag wt.)]×100

The bag correction factor is the weight of an empty, sealed bag divided by the weight of the same bag after going through the ruminal in vitro and NDF procedure. Neutral detergent fiber digestibility was determined using the following equation:

NDFD (% of NDF)=100×[($NDF_{0\ hour}$−$NDF_{residue}$)/($NDF_{0\ hour}$)]

Statistical Analysis:

The complete data set was analyzed as a randomized complete block design with subsampling using SAS Proc Mixed (SAS, Cary, N.C.). The model used was:

$Y_{ijkl}=\mu+R_i+M_j+T_k+F_l+RM_{ij}+RF_{il}+RT_{ik}+MT_{jk}+TF_{kl}+RMF_{ijl}+RTF_{ikl}+e_{ijkl}$ where; $Y_{ijkl}$=NDFD, dependent variable, μ=population mean, $R_i$=random effect of repetition i, $M_j$=fixed effect of method, T=fixed effect of time, $F_1$=random effect of feed; $RM_{ij}$=interaction between repetition and method, $RF_{il}$=interaction between repetition and feed, $RT_{ik}$=interaction between repetition and time, $MT_{jk}$=interaction between method and time, $TF_{kl}$=interaction between time and feed, $RMF_{ijl}$=interaction between repetition, method, and feed, $RTF_{ikl}$=interaction between repetition, time, and feed, and $e_{ijkl}$=random residual error, assumed to be normally distributed. The data sets were also separated by method and analyzed using SAS Proc GLM (SAS, Cary, N.C.) to obtain repetition sums of squares. The model used was:

$Y_{ijkl}=\mu+R_i+T_j+F_k+e_{ijkl}$ where; $Y_{ijkl}$=NDFD, dependent variable, μ=population mean, $R_i$=fixed effect of repetition i, $T_j$=fixed effect of time, $F_k$=fixed effect of feed, and $e_{ijkl}$=random residual error, assumed to be normally distributed. Repetition variance, or inter-assay error, was estimated with repetition sums of squares. Repetition sums of squares for each technique were compared using an F-test. Significance was declared at P<0.05. Variance within runs was evaluated using Levene's Test (Levene, 1960) where analysis of variance was performed on the absolute deviation of each observation from the median of its group. A group was specified as the triplicate observations for each method, feed, and time point combination. Significance was declared at P<0.05.

Experiment B:

This experiment was completed to determine the capability of NIRS for predicting CG ivNDFD. Fifty-four forages were dried at 60° C. for 48 h in a forced air oven and ground to pass a 1-mm Wiley mill screen (Arthur H. Thomas, Philadelphia, Pa.). The set of 54 forages were digested for 24, 30, and 48 h in duplicate within a repetition using the CG described previously. The 54 forages were not analyzed with either the UN or GV due to time and resource constraints. Each forage sample was digested in three separate repetitions and for 24, 30, and 48 h with duplicate sub-samples for each repetition and time point combination. Eighteen forages were analyzed in each repetition, with an alfalfa silage internal standard included in each repetition.

Following ivNDFD analysis of all forages, ground forage samples were packed into a cylindrical sample holder equipped with a quartz window and then scanned between 400 and 2498 nm according to the procedures of Marten et al. (1983) supra on a near-infrared reflectance spectrophotometer (model 6500; FOSS-NIR System, Silver Spring, Md.) fit with a spinning cup holder. Forage sample data included NDF, 24, 30, and 48 h ivNDFD for calibration equation development. Calibrations were computed using partial least squares regression techniques with a 2,4,4,1 math treatment and the procedures of Mentink et al. (2006). Calibration performance was evaluated using cross validation, Shenk and Westerhaus (1991), supra, where prediction error was evaluated by dividing the calibration samples into subsets (n=4) with one subset reserved for validation and the remaining subsets used for calibration. Cross validation was completed until all subsets were used for validation once. The strength of calibration performance was based on the coefficient of determination ($R^2$), the standard error of calibration (SEC), the standard error of cross validation (SECV), and 1 minus the variance ratio (1−VR).

Neutral Detergent Fiber Digestibility (NDFD, % of NDF) and digestible NDF (dNDF, % of DM) are two terms used to report in vitro digestion parameters of NDF. These terms, however, represent different calculations and associated errors. These terms should not be used interchangeably. Parameter NDFD is calculated as a percent of total NDF, and the value increases with time. The NDF assay error is included within NDFD calculation twice, once through determination of NDF content at time=0 and again in determination of NDF residue following digestion at time=t. The term dNDF is calculated as a percentage of dry matter and the value of dNDF declines with time. The dNDF term is inherently more precise because the NDF assay error is included only once in calculation. The term NDFD is used to be consistent with the value most commonly reported by commercial laboratories (National Forage Testing Association, 2008).

Results:

In Experiment A, the objective was to determine if the depression in estimates of ivNDFD observed by the present inventors (unpublished data) could be reduced by modifying the pre-inoculation primer and including the primer at a tenfold lower rate. The primer was changed from pure cellulose to a mixture of carbohydrates and urea that would be similar in chemical composition to the donor cow diet, theoretically providing substrate for proteolytic, cellulolytic and non-cellulolytic microbial populations. Rumen bacteria are known to degrade substrate synergistically. The end product of digestion by one species may be substrate for another. Cellulolytic bacteria yield cellobiose and cellodextrins following degradation for uptake by other rumen bacteria and starch-digesting bacteria degrade amylose and amylopectin as the molecules are liberated from the protein matrix by protein degrading bacteria. The hypothesis was the modified primer may yield a more robust bacterial population for in vitro digestion than the cellulose primer used in the previous Examples. The effect of the primer was also separated from the effect of allowing rumen fluid to produce 0.12 ml of gas per ml rumen fluid inoculum by comparing CG to UN.

The forage samples analyzed in vitro differed by approximately 30% units in NDF content (see Table 8).

The amount of time for the combination of 1000 ml sidearm Erlenmeyer flasks, CG or UN, to reach an average of 37.4 mm Hg varied from 1 to 3 hours. Mean ivNDFD estimates across both feeds and all time points significantly differed at 35.51 and 35.94% of NDF for the CG and GV, respectively (Table 9). This difference was most likely caused by the CG 24 h ivNDFD mean being lower (P<0.05) than the GV method. The 24 h observation was similar to what the present inventors observed previously (data not shown). However, the observed numerical difference observed in this study was approximately one-half the 2.7% unit difference in ivNDFD reported by Goeser and Combs (submitted) with cellulose priming technique. Estimated ivNDFD for CG and GV were similar at 28, 48, and 54, and CG was greater following 72 h of digestion (Table 9). In the previous Example, the depression in 24 h ivNDFD values with the primed inoculum relative to the traditional method could have been due to a greater substrate to inoculum ratio in the primed technique in vitro flasks during digestion. In the present experiment, 24h ivNDFD estimates were still slightly depressed, but ivNDFD estimated by at later time points with the CG and GV were similar.

Repetition sums of squares were reduced over ten-fold with CG compared to GV, 19.5 and 228.9 (P<0.02), respectively, and CG repetition sums of squares were numerically smaller than UN (see Table 10). These results suggest the adding a priming substrate to the rumen fluid and holding the inoculum until it generated 0.12 ml of gas per ml was more effective in reducing inter-assay error than the GV or UN methods. The results of this experiment also indicate that the reduction in intra-assay error was observed over all five digestion time points, 24, 28, 48, 54 and 72 h. It appears the CG reduced the variable nature of rumen fluid and yielded ivNDFD estimates less affected by varying inoculum activity.

TABLE 9

In vitro NDF Digestion (ivNDFD) Estimates for Three Techniques in Experiment A

| | ivNDFD[1] Technique | | | | |
| --- | --- | --- | --- | --- | --- |
| Item | GV | UN | CG | SEM[2] | P< |
| | ivNDFD, % of NDF | | | | |
| Mean[3] | 35.94$^a$ | 34.91$^c$ | 35.51$^b$ | 0.15 | 0.01 |
| Time, h | | | | | |
| 24 | 24.88$^a$ | 22.08$^c$ | 23.55$^b$ | 0.43 | |
| 28 | 28.14$^a$ | 26.42$^b$ | 28.08$^a$ | 0.40 | |
| 48 | 40.63 | 39.87 | 39.84 | 0.33 | |
| 54 | 42.05$^a$ | 41.37$^b$ | 41.53$^{ab}$ | 0.22 | |
| 72 | 43.99$^b$ | 44.83$^a$ | 44.55$^a$ | 0.16 | |

[1]ivNDFD Techniques = GV: modified Goering and Van Soest (1970), UN: rumen fluid inoculum held to standard pressure without primer, CG: Combs-Goeser ivNDFD method.
[2]SEM = Standard error of the mean.
[3]Mean = ivNDFD, % of NDF, estimate across 5 digestion time points. Means with differing superscript differ (P < 0.05).

TABLE 10

In vitro NDF Digestion (ivNDFD) Estimate Repetition Sums of Squares for Three Techniques in Experiment A

| | ivNDFD[1] Technique | | | | |
| --- | --- | --- | --- | --- | --- |
| Item | GV | UN | CG | F-value[2] | P< |
| Repetition sums of squares[3] | 228.86 | — | 19.46 | 11.76 | 0.02 |
| | 228.86 | 55.01 | — | 4.16 | 0.10 |
| | — | 55.01 | 19.46 | 2.83 | 0.17 |

[1]ivNDFD Techniques = GV: modified Goering and Van Soest (1970), UN: rumen fluid inoculum held to standard pressure without primer, CG: Combs-Goeser ivNDFD method.
[2]F-value = larger sum of squares value/smaller sum of squares value on 4, 4 degrees of freedom.
[3]Repetition Type III sum of squares = sum of squares attributed to repetition following analysis of variance.

In vitro NDFD estimates from the UN technique, in which rumen fluid was not primed but was held in the pre-inoculation flask until gas pressure reached 37 mm Hg, were not as precise as ivNDFD estimates attained by the CG method. This observation suggests that both adding a primer and allowing 0.12 ml gas production per ml rumen fluid, are necessary to achieve greatest ivNDFD precision over time.

Results of this study also indicate that pretreatment of rumen fluid did not significantly affect intra-assay error (Table 11). The mean deviations within groups for each method were not different following Levene's test. This observation is consistent with prior observations by the present inventors (unpublished data).

TABLE 11

Levene's (1960) Test for Equality of Variance for Three in vitro NDF Digestion Techniques in Experiment A

| | ivNDFD[1] Technique | | | | |
| --- | --- | --- | --- | --- | --- |
| Item | GV | UN | CG | SEM[2] | P< |
| Mean absolute deviation from median of triplicate subsamples (Levene's test), % of NDF[3] | 1.29 | 1.45 | 1.32 | 0.14 | NS |

[1]ivNDFD Techniques = GV: modified Goering and Van Soest (1970), UN: rumen fluid inoculum held to standard pressure without primer, CG: Combs-Goeser ivNDFD standardization.
[2]SEM = Standard error of the mean.
[3]Repetition mean absolute deviation from median of triplicate subsamples, % of NDF = mean following Levene's Test in which analysis of variance was completed on absolute deviations from median of each group for three ivNDFD techniques.

Two tests of analytical technique precision are presented here; the F-test of repetition sums of squares, which compares inter-assay variance, and Levene's test for inequality of variance, which assesses intra-assay error. Both inter- and intra-assay variance should be evaluated when assessing laboratory assays. Recently, in vitro assay standard error estimates from comparing ivNDFD methods were presented for least squares means from two repetitions but after analysis using a regression model that includes a term accounting for repetition variance, or inter-assay error, in the statistical model. See Hall and Mertens (2008) "In vitro fermentation vessel type and method alter fiber digestibility estimates," *J. Dairy Sci.* 91:301-307. These type of standard errors only represent intra-assay error. The results shown here suggest that with ruminal in vitro assays, inter-assay error significantly differs between in vitro techniques.

In Experiment B, the CG method was related to NIRS spectral data for a 54 forage sample set. This forage set is comparable in size to that used by De Boever et al. (1996) "Prediction of the feeding value of grass silages by chemical parameters, in vitro digestibility and near-infrared reflectance spectroscopy," *Anim. Feed Sci. Tech.* 60:103-115, to determine acceptability NIRS prediction for digestion parameters, but may be considered a small-scale, or local, calibration set. See Aastveit and Marum (1993) "Near-infrared reflectance spectroscopy: different strategies for local calibrations in analyses of forage quality," *Appl. Spectroscopy* 47:463-469. A local calibration set offers validation of the reference technique precision and may determine the potential of the reference technique for developing universal (or large-scale) NIRS calibrations. The NIRS calibration equation $R^2$-values were 0.93, 0.93 and 0.89 for 24, 30, and 48 h in vitro NDFD, respectively (Table 12). The NIRS calibration equation $R^2$-value for 48 h ivNDFD in this study is higher than previous published values for in vitro NDFD (Andres et al., 2005 and Mentink et al., 2006). Further, to our knowledge, this is the first study to show similar NIRS calibration statistics for 24, 30, and 48 h ivNDFD measurements with a diverse set of forages. No comparisons of ivNDFD NIRS calibration $R^2$-values with previous research could be made for 24 and 30 h time points, however the NIRS calibration equation statistics for 24 and 30 h are similar to 48 h and the 48 h statistics suggest improved reference technique precision.

High quality NIRS calibration equations are dependent on the precision of the analytical reference procedure used to calibrate the instrument (Mentink et al., 2006). Only precise reference techniques result in successful NIRS calibrations, hence our observed successful NIRS calibration using the CG as a reference technique for 24, 30, and 48 h ivNDFD suggest the CG offers improved precision relative to the in vitro techniques used by Andres et al. (2005) and Mentink et al. (2006). These statistics support the notion that the Combs-Goeser ivNDFD technique offers improved precision relative to modified Goering and Van Soest (1970) techniques, however a larger sample set is necessary for large-scale NIRS calibration.

TABLE 12

NDF Composition and in vitro NDF Digestibility[1] (ivNDFD) Estimate Summary Statistics for 54 Forages Used in NIRS Calibration in Experiment B

| Item | N | Mean | Minimum | Maximum | Range[2] | SD[3] |
|---|---|---|---|---|---|---|
| NDF, % of DM | 54 | 45.52 | 24.90 | 75.93 | 51.02 | 11.41 |
| 24 h ivNDFD, % of NDF | 54 | 23.22 | 0.91 | 40.84 | 39.93 | 9.49 |
| 30 h ivNDFD, % of NDF | 54 | 30.30 | 6.72 | 49.77 | 43.05 | 10.75 |
| 48 h ivNDFD, % of NDF | 54 | 44.94 | 19.45 | 67.63 | 48.18 | 11.08 |

[1]in vitro NDF digestibility = obtained using the Combs-Goeser ivNDFD method.
[2]Range = maximum minus minimum.
[3]SD = standard deviation.

Priming rumen fluid inoculum with 1.25 mg of a mixture of carbohydrates and nitrogen per ml rumen inoculum, and allowing the solution to produce 37.5 mm Hg prior to inoculation reduces inter-assay error while producing equivalent ivNDFD estimates by priming rumen fluid with a mixed primer and allowing the fluid to produce a standard amount of gas. The results suggest that by using the CG method, ivNDFD estimates are less likely to be affected by varying rumen fluid inoculum activity. The preliminary NIRS calibration equations with $R^2 > 0.89$ using the CG as a reference procedure for 24-, 30-, and 48-h ivNDFD substantiate the improvement in precision observed for the CG. See Table 13.

TABLE 13

Calibration statistics for near-infrared spectroscopy (NIRS) prediction of NDF and in vitro NDF digestibility (ivNDFD) for 54 feeds in experiment B

| | | | Calibration Statistics[1] | | | | | |
|---|---|---|---|---|---|---|---|---|
| Item | N | Mean | Est. Min | Est. Max | SEC | $R^2$ | SECV | 1 − VR |
| NDF, % of DM | 53 | 45.43 | 10.95 | 79.90 | 1.86 | 0.97 | 2.44 | 0.95 |
| 24 h ivNDFD, % of NDF | 53 | 23.12 | 0.00 | 51.78 | 2.49 | 0.93 | 3.72 | 0.85 |
| 30 h ivNDFD, % of NDF | 53 | 30.25 | 0.00 | 62.79 | 2.82 | 0.93 | 4.40 | 0.83 |
| 48 h ivNDFD, % of NDF | 53 | 44.93 | 11.86 | 77.99 | 3.57 | 0.89 | 5.01 | 0.79 |

[1]Est. Min = NIRS calibration equation estimated minimum observed value;
Est. Max = NIRS calibration equation estimated maximum observed value;
SEC = standard error of calibration;
SECV = standard error of cross validation;
1 − VR = 1 minus variance ratio.

What is claimed is:

1. A method of calibrating a spectrophotometer, the method comprising:
    (a) measuring absorbance or reflectance of an undigested plant matter sample using a spectrophotometer;
    (b) harvesting rumen fluid from at least one ruminant animal;
    (c) combining the rumen fluid with a primer composition comprising a carbohydrate; and
    (d) incubating the rumen fluid and carbohydrate of step (c) until a pre-determined endpoint is achieved, wherein the endpoint comprises a measurement selected from gas production by microbial flora in the rumen fluid, pH of the rumen fluid, or consumption of the carbohydrate in the primer composition, thereby yielding primed rumen fluid; then (e) digesting the undigested plant matter sample of step (a) with the primed rumen fluid of step (d) to yield a digested sample and measuring fiber content of the digested sample; and then (f) calibrating the spectrophotometer by correlating the measured fiber content from step (e) with the measured absorbance or reflectance from step (a).

2. The method of claim 1, wherein step (e) comprises measuring the absorbance of the plant matter sample using a near-infrared spectrophotometer.

3. The method of claim 1, wherein step (b) comprises harvesting rumen fluid from two or more bovines.

4. The method of claim 1, wherein step (c) comprises combining the rumen fluid with a primer composition comprising cellulose.

5. The method of claim 1, wherein step (c) comprises combining the rumen fluid with a primer composition comprising cellulose and one or more additional ingredients selected from the group consisting of urea, starch, cellobiose, and combinations thereof.

6. The method of claim 1, wherein step (c) comprises combining the rumen fluid with a primer composition comprising cellulose, urea, starch, and cellobiose disposed in a buffered reducing solution.

7. The method of claim 1, wherein step (c) comprises combining the rumen fluid with a primer composition comprising cellulose, urea, starch, and/or cellobiose disposed in a reducing solution comprising an aqueous solution of cysteine hydrochloride, sodium sulfide, and sodium hydroxide.

8. The method of claim 1, wherein step (d) comprises incubating the rumen fluid and carbohydrate of step (b) in a sealed vessel until a pre-determined pressure is achieved within the vessel, wherein the pre-determined pressure is the endpoint.

9. The method of claim 1, wherein step (e) comprises measuring the neutral detergent fiber content of the digested sample.

10. The method of claim 1, wherein step (e) comprises measuring the acid detergent fiber content of the digested sample.

11. A method of constructing a standard curve, the method comprising:

(a) measuring absorbance or reflectance of an undigested plant matter sample using a spectrophotometer; and (b) incubating rumen fluid from at least one ruminant animal and carbohydrate until a pre-determined endpoint is achieved, wherein the endpoint comprises a measurement selected from gas production by microbial flora in the rumen fluid, pH of the rumen fluid, or consumption of the carbohydrate in the primer composition, thereby yielding primed rumen fluid; then (c) digesting the undigested plant matter sample of step (a) with the primed rumen fluid of step (b) to yield a digested sample and measuring fiber content of the digested sample; and (d) repeating steps (a) through (c) for additional undigested plant matter samples; and then (e) constructing a standard curve by correlating the measured fiber content from step (c) with the measured absorbance or reflectance from step (a).

12. The method of claim 11, wherein step (a) comprises measuring the absorbance of the plant matter sample using a near-infrared spectrophotometer.

13. The method of claim 11, wherein step (b) comprises incubating the rumen fluid with a carbohydrate comprising cellulose.

14. The method of claim 11, wherein step (b) comprises incubating the rumen fluid with a primer composition comprising cellulose and one or more additional ingredients selected from the group consisting of urea, starch, cellobiose, and combinations thereof.

15. The method of claim 11, wherein step (b) comprises incubating the rumen fluid with a primer composition comprising cellulose, urea, starch, and cellobiose disposed in a buffered reducing solution.

16. The method of claim 11, wherein step (b) comprises incubating the rumen fluid with a primer composition comprising cellulose, urea, starch, and/or cellobiose disposed in a reducing solution comprising an aqueous solution of cysteine hydrochloride, sodium sulfide, and sodium hydroxide.

17. The method of claim 11, wherein step (b) comprises incubating the rumen fluid and carbohydrate in a sealed vessel until a pre-determined pressure is achieved within the vessel, wherein the pre-determined pressure is the endpoint.

18. The method of claim 11, wherein step (c) comprises measuring the neutral detergent fiber content of the digested sample.

19. The method of claim 11, wherein step (c) comprises measuring the acid detergent fiber content of the digested sample.

20. A standard curve for calibrating a spectrophotometer produced by a process comprising:

(a) measuring absorbance or reflectance of an undigested plant matter sample using a spectrophotometer;

(b) incubating rumen fluid from at least one ruminant animal and carbohydrate until a pre-determined endpoint is achieved, wherein the endpoint comprises a measurement selected from gas production by microbial flora in the rumen fluid, pH of the rumen fluid, or consumption of the carbohydrate in the primer composition, thereby yielding primed rumen fluid; then (c) digesting the undigested plant matter sample of step (a) with the primed rumen fluid of step (b) to yield a digested sample and measuring fiber content of the digested sample; and (d) repeating steps (a) through (c) for additional undigested plant matter samples; and then (e) constructing the standard curve by correlating the measured fiber content from step (c) with the measured absorbance or reflectance from step (a).

21. A method of measuring fiber digestion in ruminants, the method comprising:

(a) harvesting rumen fluid from at least one ruminant animal;

(b) combining the rumen fluid with a primer composition comprising a carbohydrate;

(c) incubating the rumen fluid and carbohydrate of step (b) until a pre-determined endpoint is achieved, wherein the endpoint comprises a measurement selected from gas production by microbial flora in the rumen fluid, pH of the rumen fluid, or consumption of the carbohydrate in the primer composition, thereby yielding primed rumen fluid; and then (d) digesting an undigested plant matter sample with the primed rumen fluid of step (c) to yield a digested plant matter sample and measuring fiber content of the digested plant matter sample.

22. The method of claim 21, wherein step (a) comprises harvesting rumen fluid from two or more bovines.

23. The method of claim 21, wherein step (b) comprises combining the rumen fluid with a primer composition comprising cellulose.

24. The method of claim 21, wherein step (b) comprises combining the rumen fluid with a primer composition comprising cellulose and one or more additional ingredients selected from the group consisting of urea, starch, cellobiose, and combinations thereof.

25. The method of claim 21, wherein step (b) comprises combining the rumen fluid with a primer composition comprising cellulose, urea, starch, and cellobiose disposed in a buffered reducing solution.

26. The method of claim 21, wherein step (b) comprises combining the rumen fluid with a primer composition comprising cellulose, urea, starch, and/or cellobiose disposed in a reducing solution comprising an aqueous solution of cysteine hydrochloride, sodium sulfide, and sodium hydroxide.

27. The method of claim 21, wherein step (c) comprises incubating the rumen fluid and carbohydrate of step (b) in a sealed vessel until a pre-determined pressure is achieved within the vessel, wherein the pre-determined pressure is the endpoint.

28. The method of claim 21, wherein step (d) comprises measuring the neutral detergent fiber content of the digested plant matter sample.

29. The method of claim 21, wherein step (d) comprises measuring the acid detergent fiber content of the digested plant matter sample.

* * * * *